(12) United States Patent
Morimoto et al.

(10) Patent No.: US 9,895,054 B2
(45) Date of Patent: Feb. 20, 2018

(54) ENDOSCOPE SYSTEM, LIGHT SOURCE DEVICE, OPERATION METHOD FOR ENDOSCOPE SYSTEM, AND OPERATION METHOD FOR LIGHT SOURCE DEVICE

(71) Applicant: FUJIFILM Corporation, Tokyo (JP)

(72) Inventors: Yoshinori Morimoto, Ashigarakami-gun (JP); Satoshi Ozawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 280 days.

(21) Appl. No.: 14/712,028

(22) Filed: May 14, 2015

(65) Prior Publication Data

US 2015/0366444 A1  Dec. 24, 2015

(30) Foreign Application Priority Data

Jun. 24, 2014  (JP) .................................. 2014-129714

(51) Int. Cl.
| | | |
|---|---|---|
| *A61B 5/1455* | (2006.01) | |
| *A61B 1/06* | (2006.01) | |
| *A61B 5/1459* | (2006.01) | |
| *A61B 1/00* | (2006.01) | |

(52) U.S. Cl.
CPC ........ *A61B 1/0638* (2013.01); *A61B 1/00009* (2013.01); *A61B 1/0684* (2013.01); *A61B 5/1459* (2013.01); *A61B 5/14551* (2013.01); *A61B 1/00186* (2013.01)

(58) Field of Classification Search
None
See application file for complete search history.

(56) References Cited

U.S. PATENT DOCUMENTS

2012/0157768 A1  6/2012  Saito
2015/0092035 A1  4/2015  Yamamoto et al.

FOREIGN PATENT DOCUMENTS

| JP | 2007-139822 A | 6/2007 |
| JP | 5303012 B2 | 10/2013 |
| JP | 2013-255055 A | 12/2013 |

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

An endoscope system includes a light source unit, a band limiting unit, a light source control unit, an imaging sensor, an imaging control unit, and an oxygen saturation image generation unit. The light source unit includes a V-LED that emits violet light, a B-LED that emits blue light, a G-LED that emits green light, and an R-LED that emits red light. The band limiting unit generates measurement light having a specific wavelength band for measuring the oxygen saturation from the blue light. The light source control unit switches the control of the light source unit between a first light emission mode, in which the observation target is irradiated with the violet light, the measurement light, the green light, and the red light, and a second light emission mode, in which the observation target is irradiated with the measurement light.

21 Claims, 13 Drawing Sheets

☐ LOW OXYGEN REGION

ENDOSCOPE SYSTEM, LIGHT SOURCE DEVICE, OPERATION METHOD FOR ENDOSCOPE SYSTEM, AND OPERATION METHOD FOR LIGHT SOURCE DEVICE

CROSS-REFERENCE TO RELATED APPLICATIONS

The present application claims priority under 35 U.S.C. § 119 to Japanese Patent Application No. 2014-129714, filed on Jun. 24, 2014. The above application is hereby expressly incorporated by reference, in its entirety, into the present application.

BACKGROUND OF THE INVENTION

1. Field of the Invention

The present invention relates to an endoscope system that forms illumination light for illuminating an observation target using light sources of a plurality of colors, a light source device, an operation method for an endoscope system, and an operation method for a light source device.

2. Description of the Related Art

In the medical field, diagnosis using an endoscope system including a light source device, an endoscope, and a processor device has been widely performed. The light source device is a device that generates illumination light emitted to the observation target, such as a mucosa of the body cavity. As the light source device, not only is a broadband light source, such as a xenon lamp or a white light emitting diode (LED), used, but also semiconductor light sources of a plurality of colors, such as a blue LED, a green LED, and a red LED, have been used in combination with each other in recent years.

For example, in the endoscope system disclosed in JP-2013-255655A, four semiconductor light sources that are independently controllable are mounted in a light source device. The spectrum (light intensity distribution for each wavelength) of illumination light is adjusted by controlling the amount of light emitted from each of the four semiconductor light sources, so that the observation target can be irradiated with illumination light having optimal characteristics according to image characteristics to be acquired. Specifically, in order to obtain an image having a large dynamic range for brightness, an image with a low color temperature, an image with a high color temperature, and an image when irradiating a narrow region with special narrow-band wavelength light, the spectrum of illumination light or the like is adjusted.

The endoscope system disclosed in JP-2007-139822A includes an LED that emits visible light and an LED that emits ultraviolet light. By emitting not only the visible light but also the ultraviolet light, a wound on which fluorescent paint applied in advance is accumulated becomes noticeable by the fluorescent light.

In addition, an endoscope system that acquires not only an image of the observation target but also information indicating the characteristics of the observation target has been known in recent years. For example, in the endoscope system disclosed in JP5303012B, the oxygen saturation is measured as a characteristic of the observation target by irradiating the observation target with oxygen saturation measurement light (hereinafter, referred to as measurement light) having a wavelength band in which there is a difference between the absorption coefficient of oxygenated hemoglobin and the absorption coefficient of reduced hemoglobin, and an image showing the oxygen saturation (hereinafter, referred to as an oxygen saturation image) is generated and displayed.

SUMMARY OF THE INVENTION

Also in the endoscope system using a light source device that generates illumination light by controlling the amount of light of each of the semiconductor light sources of a plurality of colors, it is desirable to be able to measure the oxygen saturation. However, since the spectrum of light emitted from each semiconductor light source cannot be adjusted just by providing the semiconductor light sources of a plurality of colors, it is difficult to measure the oxygen saturation. That is, in order to measure the oxygen saturation, it is necessary to image the observation target by emitting measurement light having a specific wavelength band in which there is a difference between the absorption coefficient of oxygenated hemoglobin and the absorption coefficient of reduced hemoglobin. However, when light other than the measurement light having a specific wavelength band is included, the measurement accuracy is reduced. In addition, even if the semiconductor light sources of a plurality of colors are mounted in the light source device, measurement light for measuring the oxygen saturation accurately cannot be obtained just by adjusting the amount of light of each of the semiconductor light sources. For this reason, it is necessary to use a band limiting unit for generating the measurement light.

However, when the band limiting unit for generating the measurement light is used, the visibility of the observation target is reduced to the same extent that a wavelength band is cut by the band limiting unit. Specifically, measurement light having a blue wavelength band is used to measure the oxygen saturation. Accordingly, the band limiting unit for generating the measurement light is disposed before the blue semiconductor light source that emits blue light. However, the blue light has a wavelength band in which the contrast is expressed mainly by fine structures near the mucosal surface, such as superficial blood vessels or a pit pattern. Therefore, the visibility of these structures may be reduced due to cutting a part of the blue light in order to generate the measurement light. In addition, when the band limiting unit for generating the measurement light is used, the amount of light for imaging also easily becomes insufficient to the same extent that a wavelength band is cut by the band limiting unit.

It is an object of the invention to provide an endoscope system that can accurately measure the oxygen saturation of an observation target and that has good visibility of fine structures, such as superficial blood vessels, a light source device, an operation method for an endoscope system, and an operation method for a light source device.

An endoscope system of the invention includes a light source unit, a band limiting unit, a light source control unit, a color imaging sensor, an imaging control unit, and an oxygen saturation image generation unit. The light source unit includes a violet light source that emits violet light, a blue light source that emits blue light, a green light source that emits green light, and a red light source that emits red light. The band limiting unit generates measurement light having a specific wavelength band for measuring oxygen saturation from the blue light. The light source control unit controls the light source unit in a first light emission mode, in which an observation target is irradiated with illumination light including the violet light, the measurement light, the green light, and the red light, and a second light emission mode, in which the observation target is irradiated with the measurement light, and controls switching between the first and second light emission modes. The color imaging sensor has a blue pixel for receiving the violet light and the measurement light, a green pixel for receiving the green light, and a red pixel for receiving the red light. The imaging control unit images the observation target with reflected light of the illumination light in the first light emission mode using the color imaging sensor and outputs a first blue image signal, a first green image signal, and a first red image signal from the color imaging sensor, and images the observation target with reflected light of the measurement light in the second light emission mode using the color imaging sensor and outputs a second blue image signal from the color imaging sensor. The oxygen saturation image generation unit calculates oxygen saturation of the observation target using the second blue image signal, and generates an oxygen saturation image showing the oxygen saturation of the observation target using the oxygen saturation, the first blue image signal, the first green image signal, and the first red image signal.

Preferably, a wavelength band of the blue light includes a wavelength at which absorption coefficients of oxygenated hemoglobin and reduced hemoglobin are the same, and the specific wavelength band of the measurement light generated by the band limiting unit is a wavelength band in which the absorption coefficient of the oxygenated hemoglobin is equal to or greater than the absorption coefficient of the reduced hemoglobin, or a wavelength band in which the absorption coefficient of the oxygenated hemoglobin is equal to or less than the absorption coefficient of the reduced hemoglobin.

Preferably, when controlling the light source unit in the second light emission mode, the light source control unit turns off the violet light source, the green light source, and the red light source, or reduces an amount of light of each of the violet light source, the green light source, and the red light source from an amount of light of each of the violet light source, the green light source, and the red light source in the first light emission mode in a state where the violet light source, the green light source, and the red light source are turned on.

Preferably, the oxygen saturation image generation unit generates the oxygen saturation image by performing structure enhancement processing for enhancing structures of the observation target, and changes a degree of the structure enhancement processing using the amount of violet light in the first light emission mode.

Preferably, the light source control unit forms white light with the measurement light, the green light, and the red light in the first light emission mode, adds the violet light to the white light, and irradiates the observation target with the white light including the violet light.

It is preferable to further include an exposure designation value calculation unit that calculates an exposure designation value for designating the amount of violet light, the amount of measurement light, the amount of green light, and the amount of red light in the first light emission mode or a storage time of the color imaging sensor using the second blue image signal.

Preferably, the exposure designation value is a value for designating the amount of blue light in the first light emission mode using the second blue image signal, and the exposure designation value calculation unit has a light amount correlation, which is obtained by associating the amount of violet light with the amount of blue light, and designates the amount of violet light using the light amount correlation and the amount of blue light designated by the exposure designation value.

Preferably, the exposure designation value is a value for designating the storage time of the color imaging sensor in the first light emission mode using the second blue image signal.

It is preferable to further include a halation detection unit that detects halation using the second blue image signal. Preferably, the exposure designation value calculation unit calculates the exposure designation value using signal values of pixels, other than a pixel in which the halation is detected, of the second blue image signal.

Preferably, the light source control unit controls the light source unit alternately between the first and second light emission modes so as to match an observation target imaging timing of the color imaging sensor.

Preferably, the oxygen saturation image generation unit calculates the oxygen saturation using a plurality of the second blue image signals.

Preferably, the oxygen saturation image generation unit generates the oxygen saturation image using a plurality of the first blue image signals, a plurality of the first green image signals, and a plurality of the first red image signals.

A light source device of the invention includes a light source unit, a band limiting unit, and a light source control unit. The light source unit includes a violet light source that emits violet light, a blue light source that emits blue light, a green light source that emits green light, and a red light source that emits red light. The band limiting unit generates measurement light having a specific wavelength band for measuring oxygen saturation from the blue light. The light source control unit controls the light source unit in a first light emission mode, in which an observation target is irradiated with the violet light, the measurement light, the green light, and the red light, and a second light emission mode, in which the observation target is irradiated with the measurement light, and controls switching between the first and second light emission modes.

Preferably, a wavelength band of the blue light includes a wavelength at which absorption coefficients of oxygenated hemoglobin and reduced hemoglobin are the same, and the specific wavelength band of the measurement light generated by the band limiting unit is a wavelength band in which the absorption coefficient of the oxygenated hemoglobin is equal to or greater than the absorption coefficient of the reduced hemoglobin or a wavelength band in which the absorption coefficient of the oxygenated hemoglobin is equal to or less than the absorption coefficient of the reduced hemoglobin.

Preferably, when controlling the light source unit in the second light emission mode, the light source control unit turns off the violet light source, the green light source, and the red light source.

Preferably, when controlling the light source unit in the second light emission mode, the light source control unit reduces an amount of light of each of the violet light source, the green light source, and the red light source from an amount of light of each of the violet light source, the green light source, and the red light source in the first light emission mode in a state where the violet light source, the green light source, and the red light source are turned on.

An operation method for an endoscope system of the invention is an operation method for an endoscope system including a light source unit that includes a violet light source that emits violet light, a blue light source that emits blue light, a green light source that emits green light, and a red light source that emits red light and a band limiting unit that generates measurement light having a specific wavelength band for measuring oxygen saturation from the blue light. The operation method for an endoscope system includes a first light source control step, a first imaging step, a second light source control step, a second imaging step, and an oxygen saturation image generation step. In the first light source control step, a light source control unit controls the light source unit in a first light emission mode in which an observation target is irradiated with illumination light including the violet light, the measurement light, the green light, and the red light. In the first imaging step, a color imaging sensor having a blue pixel for receiving the violet light and the measurement light, a green pixel for receiving the green light, and a red pixel for receiving the red light images the observation target with reflected light of the illumination light in the first light emission mode, and outputs a first blue image signal, a first green image signal, and a first red image signal. In the second light source control step, the light source control unit controls the light source unit in a second light emission mode in which the observation target is irradiated with the measurement light. In the second imaging step, the color imaging sensor images the observation target with reflected light of the measurement light in the second light emission mode and outputs a second blue image signal. In the oxygen saturation image generation step, an oxygen saturation image generation unit calculates oxygen saturation of the observation target using the second blue image signal, and generates an oxygen saturation image showing the oxygen saturation of the observation target using the oxygen saturation, the first blue image signal, the first green image signal, and the first red image signal. In addition, the second light source control step and the second imaging step may be performed after the first light source control step and the first imaging step, or the first light source control step and the first imaging step may be performed after the second light source control step and the second imaging step.

An operation method for a light source device of the invention is an operation method for a light source device including a light source unit that includes a violet light source that emits violet light, a blue light source that emits blue light, a green light source that emits green light, and a red light source that emits red light and a band limiting unit that generates measurement light having a specific wavelength band for measuring oxygen saturation from the blue light. The operation method for a light source device includes a first light source control step and a second light source control step. In the first light source control step, a light source control unit controls the light source unit in a first light emission mode in which an observation target is irradiated with the violet light, the measurement light, the green light, and the red light. In the second light source control step, the light source control unit controls the light source unit in a second light emission mode in which the observation target is irradiated with the measurement light. In addition, the execution sequence of the first light source control step and the second light source control step is arbitrary. The second light source control step may be performed after the first light source control step, or the first light source control step may be performed after the second light source control step.

In the invention, in order to measure the oxygen saturation and generate an oxygen saturation image showing the oxygen saturation, the observation target is irradiated with the illumination light in the first light emission mode, in which the observation target is irradiated with the violet light, the measurement light generated from the blue light, the green light, and the red light, and a second light emission mode, in which the observation target is irradiated with the measurement light. Therefore, when imaging the observation target with the reflected light of the illumination light in the first light emission mode to acquire the image signal as a base of the oxygen saturation image, illumination light to which the violet light is added is emitted so that the contrast of superficial blood vessels and the like is easily obtained, instead of cutting a part of the wavelength band of the blue light by generating measurement light from the blue light. As a result, it is possible to provide an endoscope system that can accurately measure the oxygen saturation of an observation target and has good visibility of fine structures, such as superficial blood vessels, a light source device, an operation method for an endoscope system, and an operation method for a light source device.

DESCRIPTION OF THE PREFERRED EMBODIMENTS

First Embodiment

Figure 1:
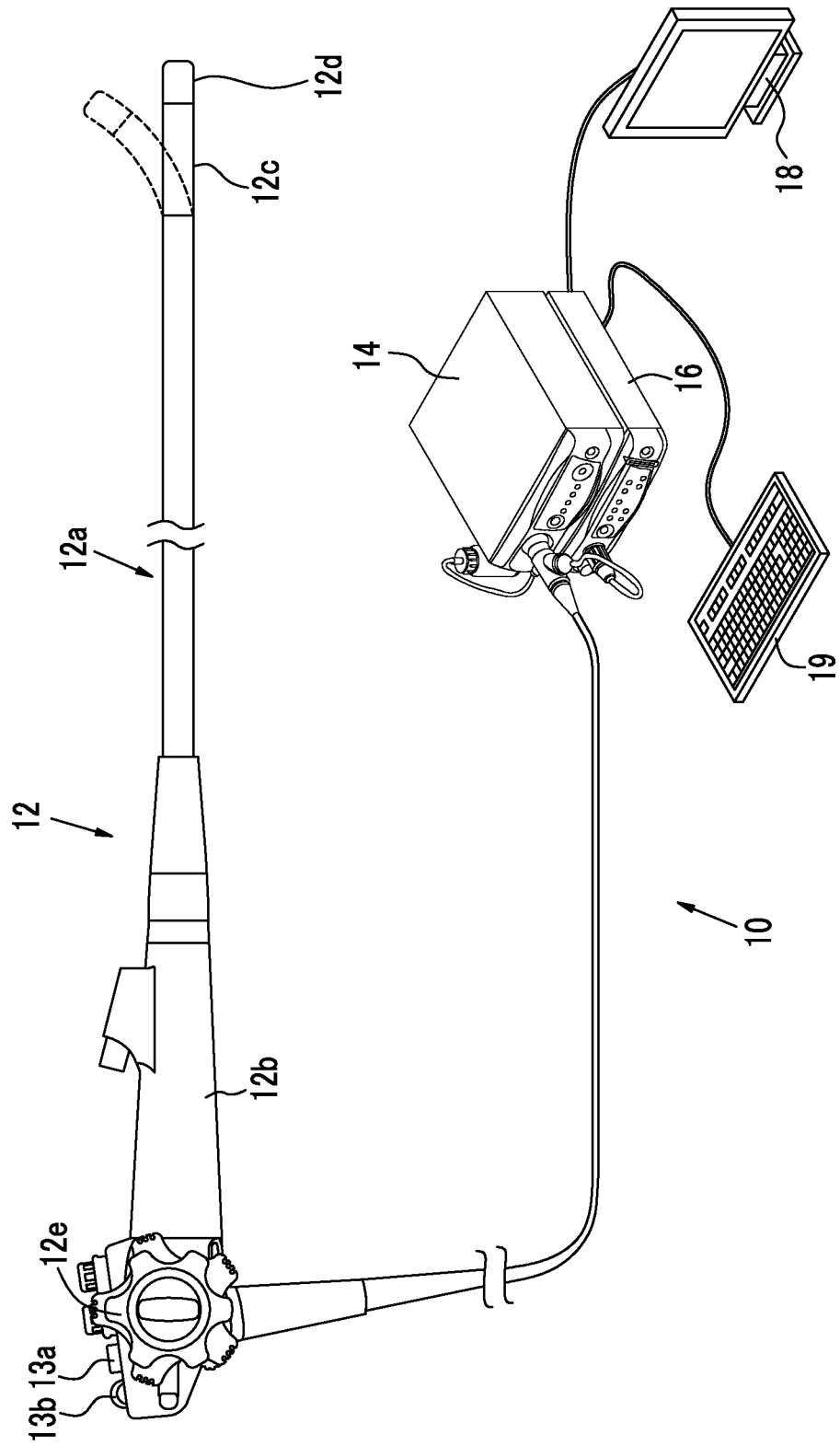
FIG. 1 is an external view of an endoscope system.

As shown in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion unit 12a that is inserted into a subject, an operating unit 12b provided at the proximal end of the insertion unit 12a, and a bending portion 12c and a distal portion 12d that are provided at the distal side of the insertion unit 12a. By operating an angle knob 12e of the operating unit 12b, the bending portion 12c is bent. Through the bending operation, the distal portion 12d is directed toward a desired direction.

In addition to the angle knob 12e, a mode selector switch (hereinafter, referred to as a mode selector SW) 13a and a zoom operation section 13b are provided in the operating unit 12b. The mode selector SW 13a is used for an observation mode switching operation. The endoscope system 10 has a normal observation mode and an oxygen saturation observation mode as observation modes. In the normal observation mode, an image of natural colors obtained by imaging using the reflected light of white light (hereinafter, referred to as a normal image) is displayed on a monitor 18. In the oxygen saturation observation mode, the oxygen saturation of the observation target is measured by irradiating the observation target with measurement light having a specific wavelength band for measuring the oxygen saturation, and an oxygen saturation image that is colored using the value of the oxygen saturation is displayed on the monitor 18.

The processor device 16 is electrically connected to the monitor 18 and the console 19. The monitor 18 outputs and displays an image of each of the observation modes and image information and the like to be attached to the image. The console 19 functions as a user interface for receiving an input operation, such as a function setting. In addition, an external recording unit (not shown) in which images or image information and the like are recorded may be connected to the processor device 16.

Figure 2:
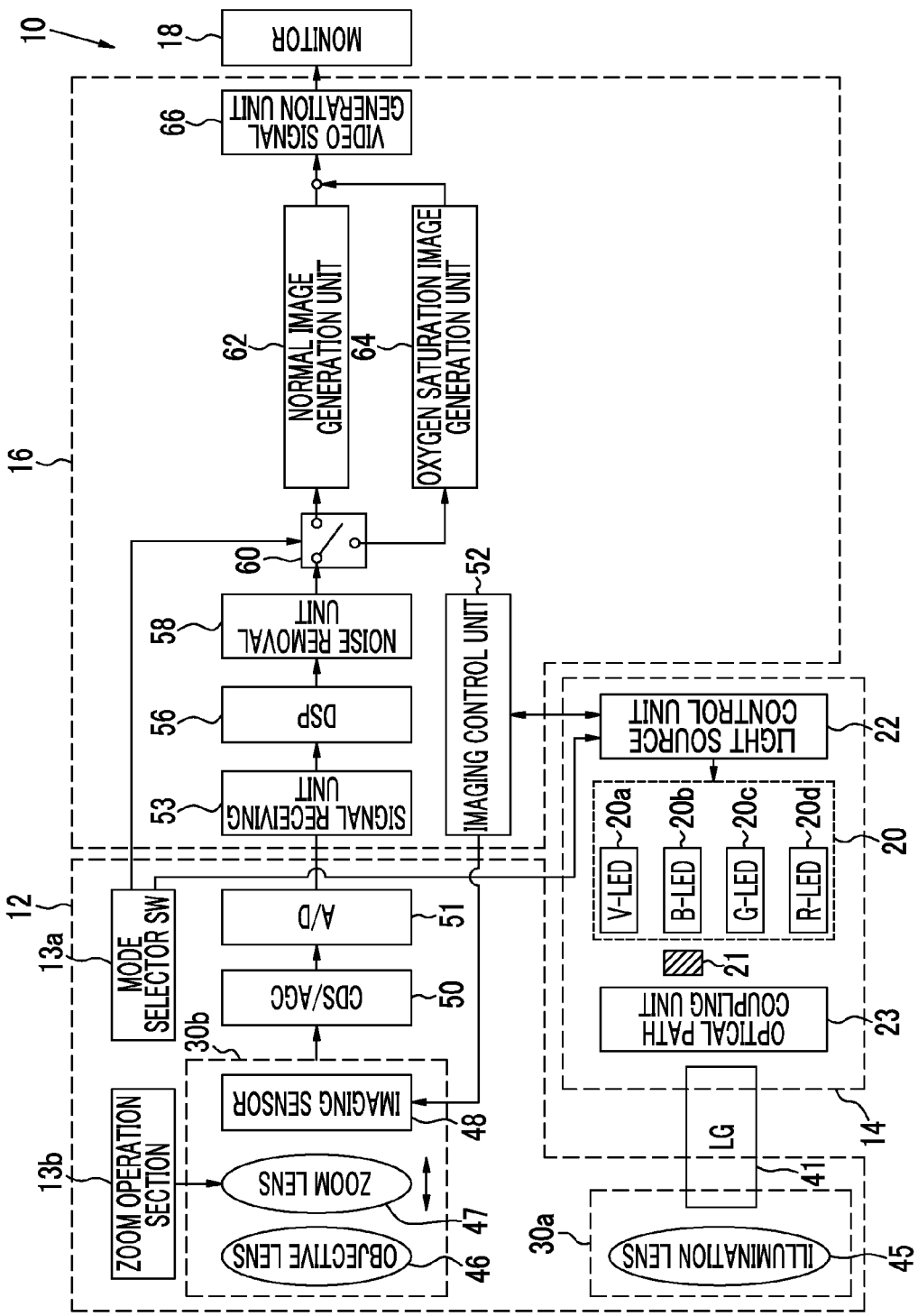
FIG. 2 is a block diagram showing the function of the endoscope system.

As shown in FIG. 2, the light source device 14 includes four semiconductor light sources, and includes a light source unit 20 that generates light emitted to the observation target, a band limiting unit 21 that limits the wavelength band of the light emitted from the light source unit 20 for each observation mode, a light source control unit 22 that controls the driving of the light source unit 20 and the band limiting unit 21, and an optical path coupling unit 23 that couples the optical paths of light components generated by the light source unit 20 and the band limiting unit 21.

Figure 3:
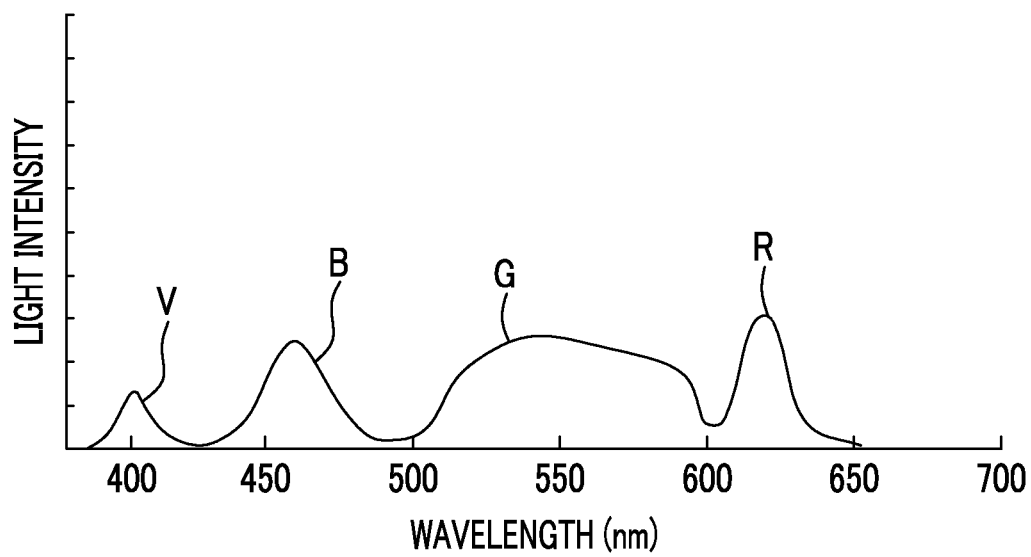
FIG. 3 is a graph showing the spectra of violet light, blue light, green light, and red light.

The light source unit 20 includes LEDs of four colors of a violet light emitting diode (V-LED) 20a, a blue light emitting diode (B-LED) 20b, a green light emitting diode (G-LED) 20c, and a red light emitting diode (R-LED) 20d. As shown in FIG. 3, the V-LED 20a is a violet light source that emits violet light V in a wavelength band of 380 nm to 420 nm that has a center wavelength of 405 nm. The B-LED 20b is a blue light source that emits blue light B in a wavelength band of 420 nm to 500 nm that has a center wavelength of 460 nm. The G-LED 20c is a green light source that emits green light G in a wavelength band of 480 nm to 600 nm. The R-LED 20d is a red light source that emits red light R in a wavelength band of 600 nm to 650 nm that has a center wavelength of 620 nm to 630 nm. In addition, the width of the center wavelength of each of the V-LED 20a and the B-LED 20b is about ±5 nm to ±10 nm.

Figure 4:
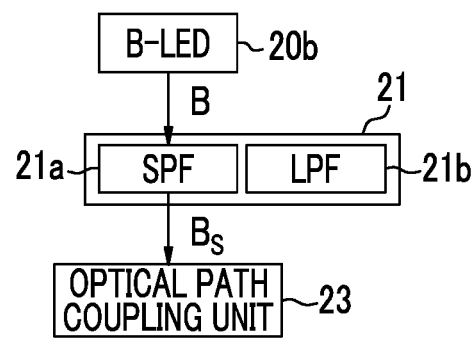
FIG. 4 is an explanatory diagram showing the configuration of a band limiting unit.

The band limiting unit 21 is provided on the optical path of the B-LED 20b, and generates light having a specific wavelength band from the blue light emitted from the B-LED 20b. Specifically, as shown in FIG. 4, the band limiting unit 21 includes a short pass filter (SPF) 21a and a long pass filter (hereinafter, referred to as an LPF) 21b, and these are freely switched according to the selected observation mode. Switching between the SPF 21a and LPF 21b is controlled by the light source control unit 22.

Figure 5:
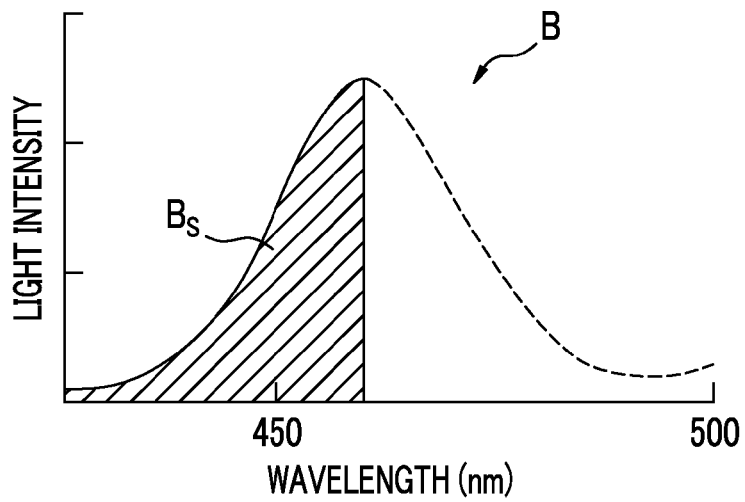
FIG. 5 is a graph showing the spectrum of blue light for normal observation.
Figure 6:
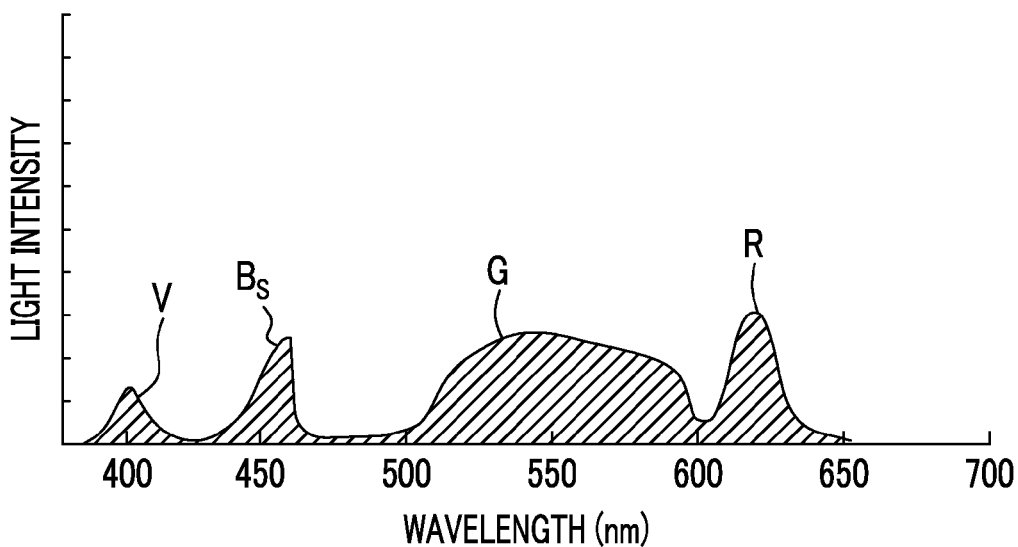
FIG. 6 is a graph showing the spectrum of illumination light in a normal observation mode.

As shown in FIG. 5, the SPF 21a is disposed on the optical path of the B-LED 20b (for example, on the front of the B-LED) in the normal observation mode. The SPF 21a transmits light having a wavelength band (wavelength of 460 nm or less) on the short wavelength side and cuts a wavelength band (wavelength of 460 nm or more) on the long wavelength side with the peak wavelength of the blue light B emitted from the B-LED 20b as a boundary. That is, the SPF 21a generates blue light for a normal observation mode (hereinafter, referred to as blue light for normal observation) $B_S$ from the blue light B. In the normal observation mode, the light source control unit 22 turns on all of the V-LED 20a, the B-LED 20b, the G-LED 20c, and the R-LED 20d. Accordingly, in the normal observation mode, as shown in FIG. 6, the blue light for normal observation $B_S$, the green light G, and the red light R are coupled by the optical path coupling unit 23, and are emitted to the observation target as illumination light. The illumination light including the blue light for normal observation $B_S$, the green light G, and the red light R is almost white light (hereinafter, referred to as white light for normal observation). The reason why the blue light for normal observation $B_S$ is generated from the blue light B in the normal observation mode as described above is that the light in a wavelength band of 460 nm to 500 nm lowers the contrast of structures, such as superficial blood vessels or a pit pattern.

In the present embodiment, in the normal observation mode, the V-LED 20a is turned on to irradiate the observation target with the white light for normal observation including the violet light V. However, the V-LED 20a may be turned off in the normal observation mode. In addition, the SPF 21a cuts the blue light B schematically at a wavelength of 460 nm. However, the SPF 21a has an actual cutting characteristic in which the wavelength width is about 5 nm to 10 nm. For this reason, in order to cut the wavelength of 460 nm or more, the SPF 21a has a characteristic in which the transmissivity is attenuated from the vicinity of a wavelength of 450 nm. In order to maintain the color rendering properties for a xenon light source, it is preferable that there is no discrete wavelength band in the spectrum of illumination light emitted to the observation target. Therefore, the SPF 21a has a cutting characteristic of reducing the amount of light in a wavelength band of 460 nm or more to the extent that the color rendering properties for the xenon light source can be maintained rather than reducing the amount of light in the wavelength band of 460 nm or more of the blue light B strictly to zero. For this reason, even if the SPF 21a is used, there is no discrete wavelength band in the illumination light emitted to the observation target (refer to FIG. 6).

Figure 7:
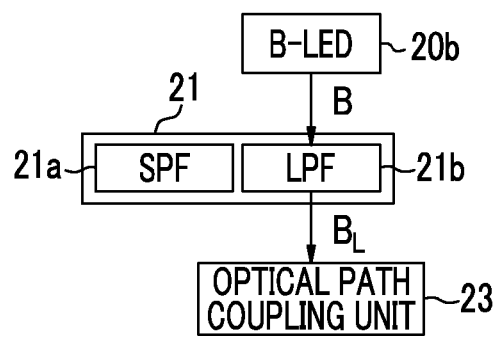
FIG. 7 is an explanatory diagram showing the arrangement of a band limiting unit in an oxygen saturation observation mode.
Figure 8:
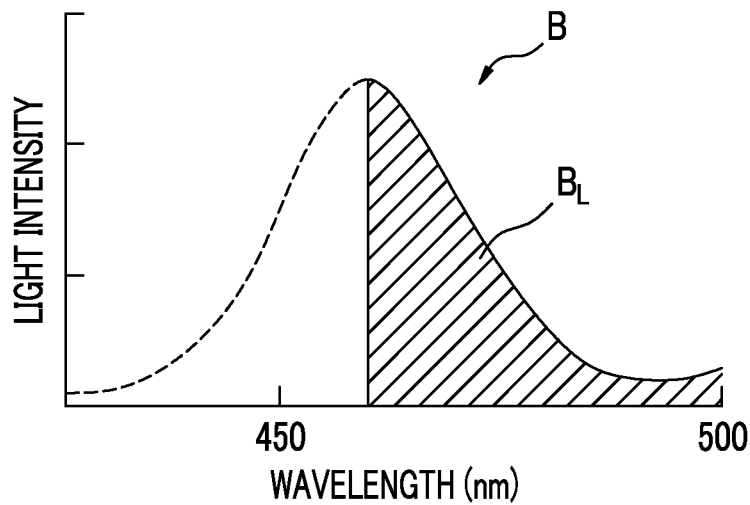
FIG. 8 is a graph showing the spectrum of measurement light.

As shown in FIG. 7, the LPF 21b is disposed on the optical path of the B-LED 20b in the oxygen saturation observation mode. In addition, as shown in FIG. 8, the LPF 21b cuts light having a wavelength band on the short wavelength side and transmits light having a wavelength band on the long wavelength side with the peak wavelength of the blue light B emitted from the B-LED 20b as a boundary. That is, the LPF 21b generates measurement light $B_L$ having a specific wavelength band for measuring the oxygen saturation from the blue light B.

Figure 9:
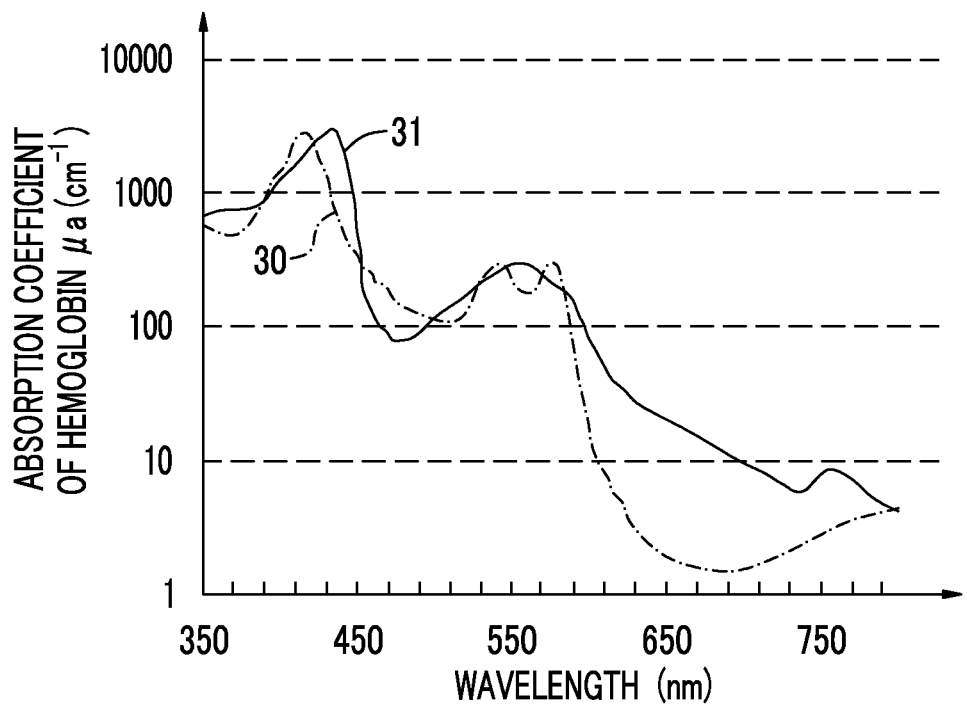
FIG. 9 is a graph showing the absorption coefficients of oxygenated hemoglobin and reduced hemoglobin.

The specific wavelength band for measuring the oxygen saturation is a wavelength band in which there is a difference between the absorption coefficient of oxygenated hemoglobin and the absorption coefficient of reduced hemoglobin to the extent that a difference in the amount of light absorption according to the oxygen saturation occurs. As shown in FIG. 9, the magnitude relationship between the absorption coefficient (graph 30) of oxygenated hemoglobin and the absorption coefficient (graph 31) of reduced hemoglobin differs depending on the wavelength band. The magnitude relationship may be reversed in multiple wavelength bands. For example, in the wavelength band from purple to blue, wavelengths at which the absorption coefficient of oxygenated hemoglobin and the absorption coefficient of reduced hemoglobin are the same are about 420 nm, about 450 nm, and about 500 nm. In the wavelength band of 420 nm to 450 nm, the absorption coefficient of oxygenated hemoglobin is smaller than the absorption coefficient of reduced hemoglobin. In the wavelength band of 450 nm to 500 nm, the absorption coefficient of oxygenated hemoglobin is larger than the absorption coefficient of reduced hemoglobin.

All of these wavelength bands can be used as specific wavelength bands for measuring the oxygen saturation. In the present embodiment, since the B-LED 20b emits the blue light B in the wavelength band of 420 nm to 500 nm, the LPF 21b transmits light having a wavelength of 460 nm or more to generate the measurement light $B_L$. Therefore, the measurement light $B_L$ has a wavelength band of 460 nm to 500 nm in which the absorption coefficient of oxygenated hemoglobin is equal to or less than the absorption coefficient of reduced hemoglobin. If the SPF that transmits light having a wavelength band of 450 nm or less is used instead of the LPF 21b, the wavelength band of the measurement light $B_L$ can be set to an wavelength band of 420 nm to 450 nm in which the absorption coefficient of oxygenated hemoglobin is equal to or greater than the absorption coefficient of reduced hemoglobin.

The blue light B emitted from the B-LED 20b includes a wavelength (isosbestic point) at which the absorption coefficient of oxygenated hemoglobin and the absorption coefficient reduced hemoglobin are the same. Therefore, the blue light B includes both of the wavelength band in which the absorption coefficient of oxygenated hemoglobin is equal to or greater than the absorption coefficient of reduced hemoglobin and the wavelength band in which the absorption coefficient of oxygenated hemoglobin is equal to or less than the absorption coefficient of reduced hemoglobin. For this reason, when the blue light B itself is used as measurement light for measuring the oxygen saturation, the measurement accuracy is low, even though the oxygen saturation can be measured. Therefore, as described above, the band limiting unit 21 generates the measurement light $B_L$ having either a wavelength band in which the absorption coefficient of oxygenated hemoglobin is equal to or less than the absorption coefficient of reduced hemoglobin or a wavelength band in which the absorption coefficient of oxygenated hemoglobin is equal to or greater than the absorption coefficient of reduced hemoglobin.

In the present embodiment, the LPF 21b cuts light having a wavelength less than 460 nm schematically. However, it is preferable that the LPF 21b has a characteristic in which the transmissivity is attenuated from the vicinity of a wavelength of, for example, 460 nm in order to cut light having a wavelength less than 450 nm, even though the LPF 21b has an actual cutting characteristic in which the wavelength width is about 5 nm to 10 nm similar to the SPF 21a. This is because the isosbestic point, at which the absorption coefficient of oxygenated hemoglobin and the absorption coefficient of reduced hemoglobin are the same, is at the wavelength of 450 nm as described above. Thus, since the LPF 21b has a characteristic of cutting light having a wavelength less than 450 nm, it is possible to use measurement light for the calculation of oxygen saturation without wasting the measurement light and to calculate the accurate oxygen saturation.

Figure 10:
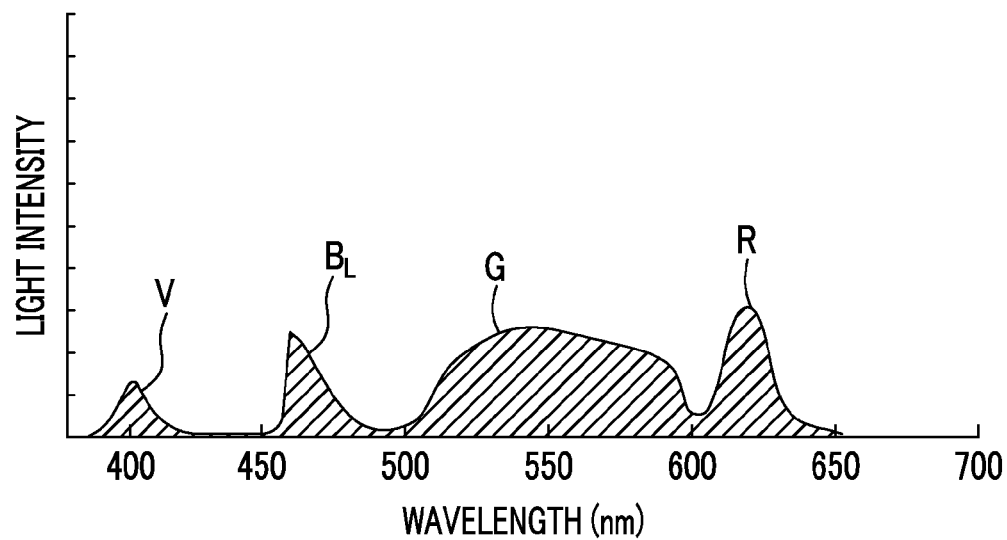
FIG. 10 is a graph showing the spectrum of illumination light emitted in a first light emission mode.

In the oxygen saturation observation mode, the light source control unit 22 controls the light source unit 20 in first and second light emission modes. That is, the light source control unit 22 performs control for switching between the first and second light emission modes. The first light emission mode is a light emission mode for irradiating the observation target with almost white light as in the normal observation mode, and the light source control unit 22 turns on all of the LEDs 20a to 20d of four colors. Accordingly, in the first light emission mode, as shown in FIG. 10, the violet light V, the measurement light $B_L$ generated from the blue light B by the LPF 21b, the green light G, and the red light R are coupled by the optical path coupling unit 23, and are emitted to the observation target as illumination light.

Although the illumination light emitted to the observation target in the first light emission mode is almost white light (hereinafter, referred to as white light for oxygen saturation observation) including the violet light V, the measurement light $B_L$, the green light G, and the red light R as described above, the illumination light emitted to the observation target in the first light emission mode has a different spectrum from the white light for normal observation (refer to FIG. 6) in the normal observation mode. Specifically, the white light for oxygen saturation observation includes the measurement light $B_L$ and the violet light V as a blue component, while the white light for normal observation includes the blue light for normal observation $B_S$, which has a wavelength band in which the contrast of structures such as superficial blood vessels is good, as a blue component. That is, since the white light for oxygen saturation observation includes the measurement light $B_L$ having a wavelength band in which the contrast of superficial blood vessels and the like is poor, as a blue component, in order to measure the oxygen saturation, the contrast of superficial blood vessels and the like is improved by adding the violet light V instead of the measurement light $B_L$. In addition, the LPF 21b has a characteristic of reducing the amount of light in a wavelength band less than 450 nm to the extent that the color rendering properties for the xenon light source can be maintained in the first light emission mode rather than reducing the amount of light in the wavelength band less than 450 nm of the blue light B strictly to zero. For this reason, even if the LPF 21b is used, there is no discrete wavelength band in the illumination light emitted to the observation target in the first light emission mode (refer to FIG. 10).

Figure 11:
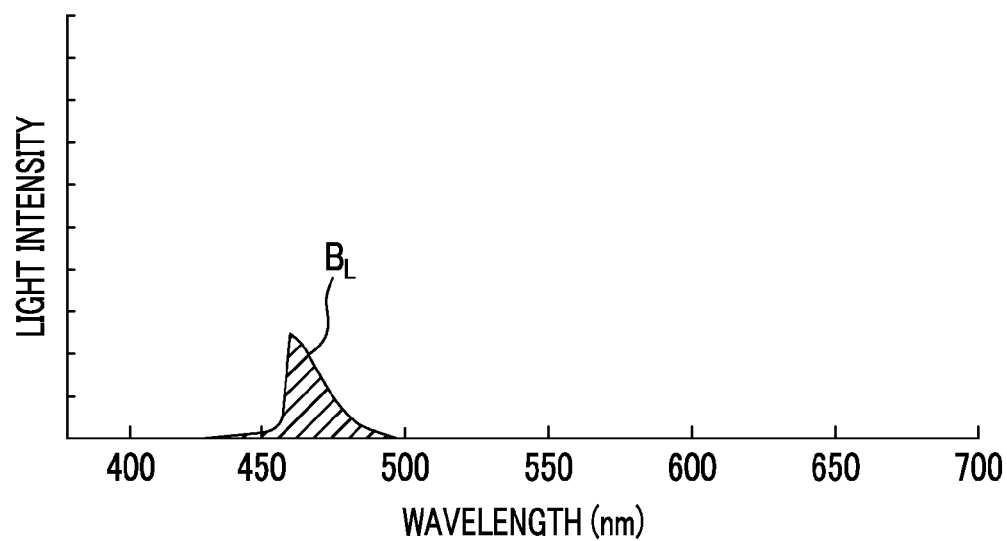
FIG. 11 is a graph showing the spectrum of illumination light emitted in a second light emission mode.

The second light emission mode is a light emission mode for measuring the oxygen saturation, and the light source control unit 22 turns on the B-LED 20b and turns off the V-LED 20a, the G-LED 20c, and the R-LED 20d. As a result, as shown in FIG. 11, in the second light emission mode, the measurement light $B_L$ is emitted to the observation target as illumination light.

The various kinds of illumination light generated as described above are incident on a light guide 41 inserted into the insertion unit 12a through the optical path coupling unit 23. The light guide 41 is built into the endoscope 12 and a universal cord (cord for connecting the endoscope 12 to the light source device 14 and the processor device 16), and makes the illumination light guided from the optical path coupling unit 23 propagate to the distal portion 12d of the endoscope 12. As the light guide 41, a multi-mode fiber can be used. As an example, it is possible to use a small-diameter fiber cable having a core diameter of 105 μm, a cladding diameter of 125 μm, and a diameter of ϕ0.3 mm to ϕ0.5 mm when a protective layer as an outer skin is included.

An illumination optical system 30a and an imaging optical system 30b are provided in the distal portion 12d of the endoscope 12. The illumination optical system 30a includes an illumination lens 45, and the illumination light propagated by the light guide 41 is emitted to the observation target through the illumination lens 45. The imaging optical system 30b includes an objective lens 46, a zoom lens 47, and an imaging sensor 48. Reflected light from the observation target is incident on the imaging sensor 48 through the objective lens 46 and the zoom lens 47. Then, a reflected image of the observation target is formed on the imaging sensor 48. The zoom lens 47 is moved freely between the telephoto end and the wide end by operating the zoom operation section 13b, thereby enlarging or reducing the reflected image of the observation target formed on the imaging sensor 48.

Figure 12:
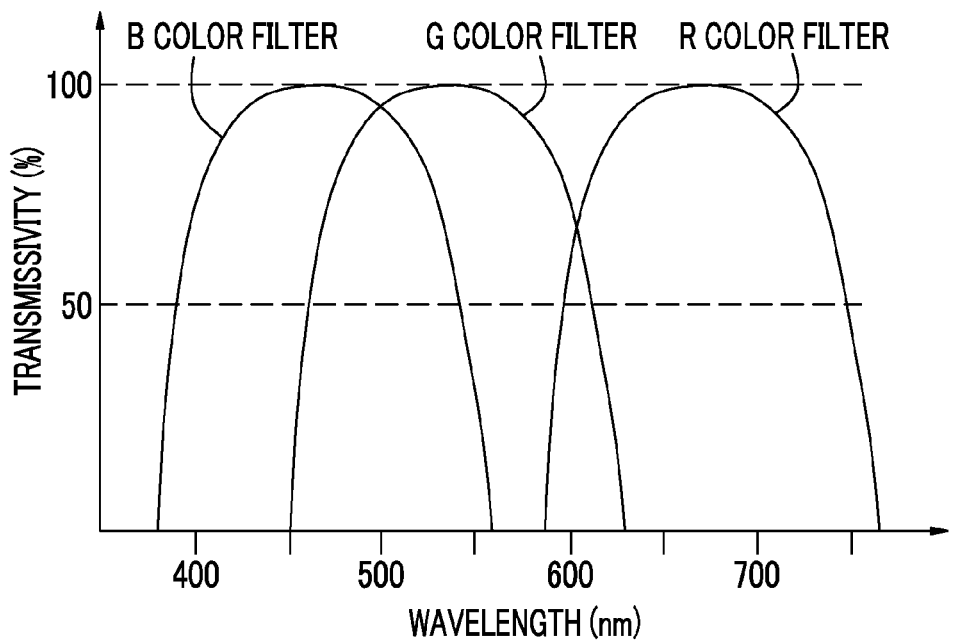
FIG. 12 is a graph showing the spectral characteristics of a color filter.

The imaging sensor 48 is a color imaging sensor, and captures the reflected image of the observation target and outputs an image signal. As the imaging sensor 48, it is possible to use a charge coupled device (CCD) imaging sensor or a complementary metal oxide semiconductor (CMOS) imaging sensor. In the imaging sensor 48, color filters of three colors of a red (R) color filter, a green (G) color filter, and a blue (B) color filter shown in FIG. 12 are provided for each pixel. The imaging sensor 48 captures a reflected image of the observation target, and outputs an image signal of each color. That is, the imaging sensor 48 has an R pixel (red pixel) in which the R color filter is provided, a G pixel (green pixel) in that the G color filter is provided, and a B pixel (blue pixel) in that the B color filter is provided, and outputs an RGB image signal by outputting an image signal from each pixel.

More specifically, as shown in Table 1, in the normal observation mode, the white light for normal observation is emitted to the observation target. Accordingly, the imaging sensor 48 receives the reflected light of the violet light V and the blue light for normal observation $B_S$ in the white light for normal observation using the B pixel, and outputs a blue image signal (hereinafter, referred to as a B image signal). Similarly, the imaging sensor 48 receives the reflected light of the green light G in the white light for normal observation using the G pixel and outputs a green image signal (hereinafter, referred to as a G image signal), and receives the reflected light of the red light R in the white light for normal observation using the R pixel and outputs a red image signal (hereinafter, referred to as an R image signal).

TABLE 1

|  | Components of illumination light | | |
| --- | --- | --- | --- |
|  | V, $B_s$ | G | R |
| Light receiving pixel | B pixel | G pixel | R pixel |
| Output image signal | B image signal | G image signal | R image signal |

As shown in Table 2, in the oxygen saturation observation mode, when the light source control unit 22 controls the light source unit 20 in the first light emission mode, the white light for oxygen saturation observation is emitted to the observation target. Accordingly, the imaging sensor 48 receives the reflected light of the violet light V and the measurement light $B_L$ in the white light for oxygen saturation observation using the B pixel, and outputs a first blue image signal (hereinafter, referred to as a B1 image signal). Similarly, the imaging sensor 48 receives the reflected light of the green light G in the white light for oxygen saturation observation using the G pixel and outputs a first green image signal (hereinafter, referred to as a G1 image signal), and receives the reflected light of the red light R in the white light for oxygen saturation observation using the R pixel and outputs a first red image signal (hereinafter, referred to as an R1 image signal).

TABLE 2

|  | Components of illumination light | | |
| --- | --- | --- | --- |
|  | V, $B_L$ | G | R |
| Light receiving pixel | B pixel | G pixel | R pixel |
| Output image signal | B1 image signal | G1 image signal | R1 image signal |

As shown in Table 3, in the oxygen saturation observation mode, when the light source control unit 22 controls the light source unit 20 in the second light emission mode, the measurement light $B_L$ is emitted to the observation target. Accordingly, the imaging sensor 48 receives the reflected light of the measurement light $B_L$ using the B pixel, and outputs a second blue image signal (hereinafter, referred to as a B2 image signal). Although the imaging sensor 48 can also output the second green image signal from the G pixel and output the second red image signal from the R pixel in the second light emission mode, the imaging sensor 48 outputs only the B2 image signal in the present embodiment since the second green image signal and the second red image signal are not used for the calculation of the oxygen saturation or the generation of the oxygen saturation image.

TABLE 3

|  | Components of illumination light $B_L$ |
| --- | --- |
| Light receiving pixel | B pixel |
| Output image signal | B2 image signal |

Instead of the imaging sensor 48, that is a color imaging sensor of primary colors, it is also possible to use a complementary color imaging sensor including complementary color filters of C (cyan), M (magenta), Y (yellow), and G (green). In the case of using the complementary color imaging sensor, image signals of four colors of CMYG are output. Therefore, by converting the image signals of four colors of CMYG into image signals of three colors of RGB by complementary color-primary color conversion, it is possible to obtain the same RGB image signals as in the imaging sensor 48. Instead of the imaging sensor 48, it is also possible to use a monochrome sensor in which no color filter is provided. In this case, the light source control unit 22 turns on the violet light V, the blue light B, the green light G, and the red light R in a time-division manner when necessary. Here, since both of the violet light V and the measurement light $B_L$ are received by the B pixel, the violet light V and the blue light B may be simultaneously turned on.

The image signal output from the imaging sensor 48 is transmitted to a CDS/AGC circuit 50. The CDS/AGC circuit 50 performs correlated double sampling (CDS) or automatic gain control (AGC) for the image signal that is an analog signal. The image signal transmitted through the CDS/AGC circuit 50 is converted into a digital image signal by an A/D converter 51. The digital image signal after A/D conversion is input to the processor device 16.

The processor device 16 includes an imaging control unit 52, a signal receiving unit 53, a digital signal processor (DSP) 56, a noise removal unit 58, an image processing switching unit 60, a normal image generation unit 62, an oxygen saturation image generation unit 64, and a video signal generation unit 66.

The imaging control unit 52 controls the observation target imaging timing of the imaging sensor 48 or the output of the image signal from the imaging sensor 48. Specifically, the imaging control unit 52 receives a synchronization signal from the light source control unit 22 (or inputs a synchronization signal to the light source control unit 22), and makes the imaging sensor 48 image an observation target with the reflected light of the illumination light in the first light emission mode and output the B1 image signal, the G1 image signal, and the R1 image signal. In addition, the imaging control unit 52 receives a synchronization signal from the light source control unit 22 (or inputs a synchronization signal to the light source control unit 22), and makes the imaging sensor 48 image an observation target with the reflected light of the measurement light $B_L$ in the second light emission mode and output the B2 image signal. The signal receiving unit 53 receives digital RGB image signals from the endoscope 12.

The DSP 56 performs various kinds of signal processing, such as defect correction processing, offset processing, gain correction processing, linear matrix processing, gamma conversion processing, and demosaic processing, on the received image signals. By the defect correction processing, the signal of the defective pixel of the imaging sensor 48 is corrected. In the offset processing, a dark current component is removed from the RGB image signals subjected to the defect correction processing, and the exact zero level is set. In the gain correction processing, the signal level is adjusted by multiplying each of the RGB image signals after the offset processing by a specific gain. Linear matrix processing for increasing color reproducibility is performed on the RGB image signals after the gain correction processing. Then, the brightness or saturation is adjusted by gamma conversion processing. Demosaic processing (also referred to as isotropic processing or synchronization processing) is performed on the RGB image signals after the linear matrix processing, and the signal of missing color in each pixel is generated by interpolation. Through the demosaic processing, all pixels have signals of RGB colors.

The noise removal unit 58 removes noise from the RGB image signals by performing noise removal processing (based on, for example, a moving average method or a median filter method) on the RGB image signals subjected to the demosaic processing or the like by the DSP 56. The RGB image signals after removing noise is transmitted to the image processing switching unit 60. The image processing switching unit 60 transmits the RGB image signals to the normal image generation unit 62 when the normal observation mode is set by the mode selector SW 13a, and transmits the RGB image signals to the oxygen saturation image generation unit 64 when the oxygen saturation observation mode is set.

The normal image generation unit 62 operates when the normal observation mode is set, and generates a normal image by performing color conversion processing, color enhancement processing, and structure enhancement processing on the RGB image signals. In the color conversion processing, color conversion processing, such as 3×3 matrix processing, gradation conversion processing, and three-dimensional look-up table (LUT) processing, is performed on the RGB image signals. The color enhancement processing is performed on the RGB image signals after the color conversion processing. The structure enhancement processing is a process for enhancing the structures of the observation target, such as superficial blood vessels or a pit pattern, and is performed on the RGB image signals after the color enhancement processing. As described above, the color image using the RGB image signals subjected to various kinds of image processing up to the structure enhancement processing is a normal image.

Figure 13:
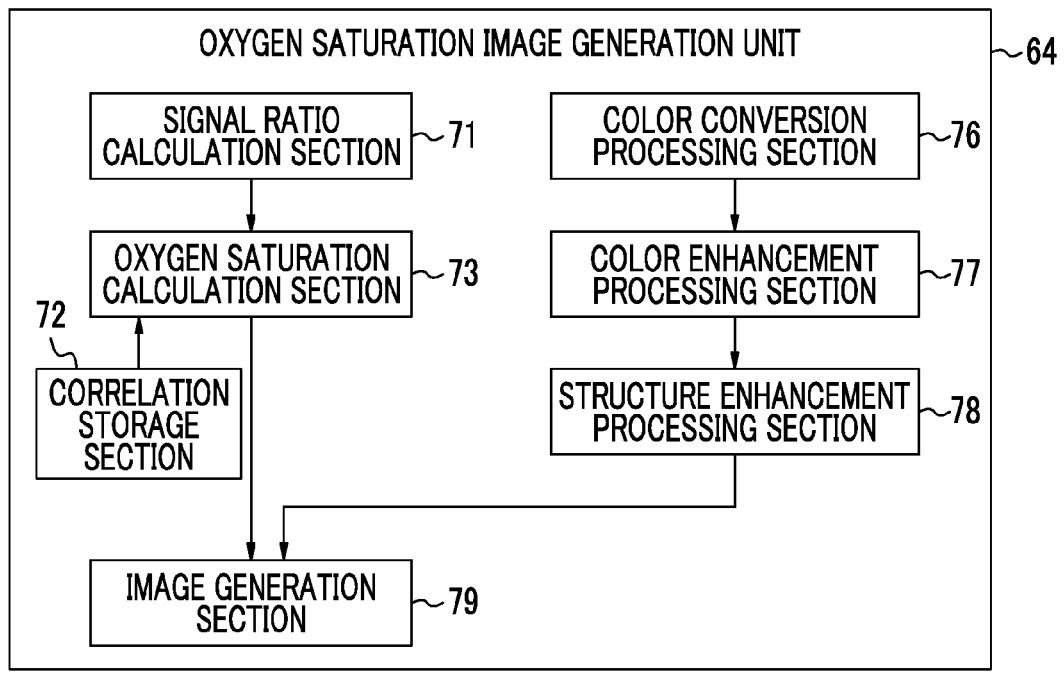
FIG. 13 is a block diagram showing the function of an oxygen saturation image generation unit.

As shown in FIG. 13, the oxygen saturation image generation unit 64 includes a signal ratio calculation section 71, a correlation storage section 72, an oxygen saturation calculation section 73, a color conversion processing section 76, a color enhancement processing section 77, a structure enhancement processing section 78, and an image generation section 79.

The signal ratio calculation section 71 calculates a signal ratio used when the oxygen saturation calculation section 73 calculates the oxygen saturation. Specifically, the signal ratio calculation section 71 calculates a ratio between the B2 image signal obtained by imaging the observation target with the reflected light of measurement light in the second light emission mode and the G1 image signal obtained by imaging the observation target with the reflected light of illumination light in the first light emission mode (hereinafter, referred to as a signal ratio B2/G1) for each pixel. In addition, the signal ratio calculation section 71 calculates a ratio between the R1 image signal and the G1 image signal obtained by imaging the observation target with the reflected light of illumination light in the first light emission mode (hereinafter, referred to as a signal ratio R1/G1) for each pixel.

Figure 14:
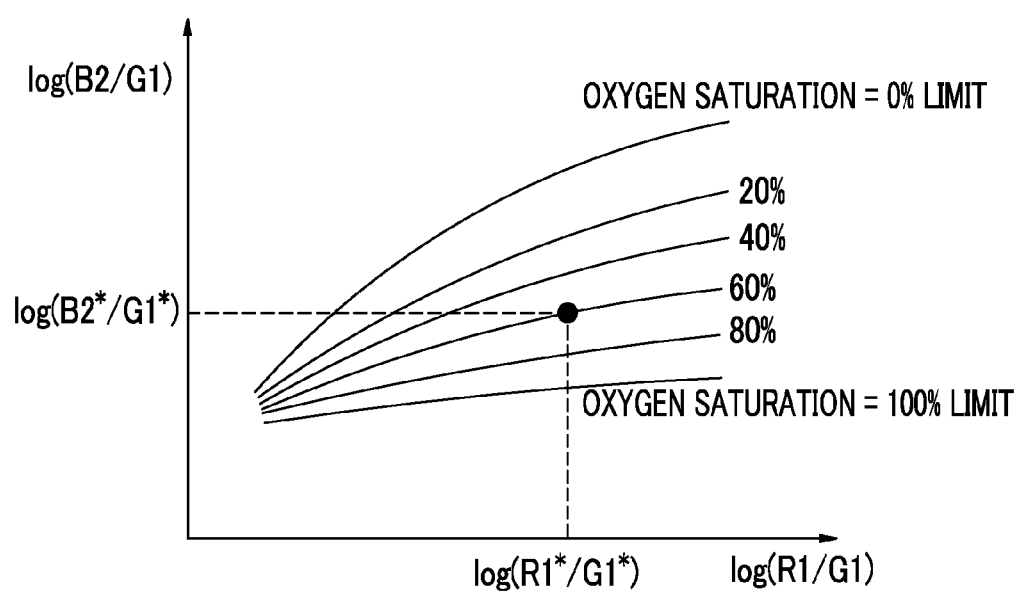
FIG. 14 is a graph showing the correlation between the signal ratio and the oxygen saturation.

The correlation storage section 72 stores the correlation between each signal ratio calculated by the signal ratio calculation section 71 and the oxygen saturation. As shown in FIG. 14, this correlation is stored in a two-dimensional table that defines the isolines of oxygen saturation in a two-dimensional space. The position and shape of each isoline for the signal ratio are obtained in advance by physical simulation of light scattering. The distance between the isolines changes according to the signal ratio R1/G1 indicating the blood volume. In addition, the correlation between the signal ratio and the oxygen saturation is stored in a log scale.

This correlation is closely related to the light scattering characteristics (refer to FIG. 9) or the absorption characteristics of oxygenated hemoglobin or reduced hemoglobin. In the wavelength band of the measurement light $B_L$ in which the difference between the absorption coefficient of oxygenated hemoglobin and the absorption coefficient of reduced hemoglobin is large, it is easy to handle the information of oxygen saturation. However, the B2 image signal, corresponding to the measurement light $B_L$, greatly depends on the blood volume as well as the oxygen saturation. Therefore, by using the signal ratio R1/G1, which is calculated from the G1 image signal that changes mainly depending on the blood volume and the R1 image signal having a low dependency on the oxygen saturation and the blood volume, in addition to the B2 image signal, it is possible to accurately calculate the oxygen saturation without there being dependency on the blood volume.

The oxygen saturation calculation section 73 calculates the oxygen saturation corresponding to the signal ratio B2/G1 and the signal ratio R1/G1 calculated by the signal ratio calculation section 71 with reference to the correlation stored in the correlation storage section 72. For example, when the signal ratio in a specific pixel is B2*/G1* and R1*/G1*, the oxygen saturation corresponding thereto is "60%" if the correlation is referred to (refer to FIG. 14). Accordingly, the oxygen saturation calculation section 73 calculates the oxygen saturation of the specific pixel as "60%".

In addition, a case where the signal ratio B2/G1 and the signal ratio R1/G1 become extremely large or extremely small rarely occurs. That is, a case rarely occurs in which the combination of the signal ratio B2/G1 and the signal ratio R1/G1 exceeds the lower limit isoline indicating the oxygen saturation of 0% or becomes lower than the upper limit isoline indicating the oxygen saturation of 100%. Here, the oxygen saturation calculation section 73 calculates the oxygen saturation as 0% when the calculated oxygen saturation is lower than the lower limit isoline, and calculates the oxygen saturation as 100% when the calculated oxygen saturation exceeds the upper limit isoline.

As described above, the oxygen saturation is calculated. On the other hand, the oxygen saturation image generation unit 64 generates an image as a base (hereinafter, referred to as a base image) of the oxygen saturation image using the color conversion processing section 76, the color enhancement processing section 77, and the structure enhancement processing section 78. The color conversion processing section 76 performs color conversion processing, such as 3×3 matrix processing, gradation conversion processing, and three-dimensional LUT processing, on the B1 image signal, the G1 image signal, and the R1 image signal obtained by imaging the observation target with the reflected light of the illumination light in the first light emission mode. The color enhancement processing section 77 performs color enhancement processing on the B1 image signal, the G1 image signal, and the R1 image signal after the color conversion processing. The structure enhancement processing section 78 performs structure enhancement processing for enhancing the structures of the observation target, such as superficial blood vessels or a pit pattern, on the B1 image signal, the G1 image signal, and the R1 image signal after the color enhancement processing. That is, the base image is formed by the B1 image signal, the G1 image signal, and the R1 image signal subjected to various kinds of image processing that are the same as in the normal image generation unit 62.

The image generation section 79 generates an oxygen saturation image showing the oxygen saturation of the observation target using the oxygen saturation calculated by the oxygen saturation calculation section 73 and the B1 image signal, the G1 image signal, and the R1 image signal subjected to the various kinds of image processing described above. Specifically, the image generation section 79 multiplies each of the B1 image signal, the G1 image signal, and the R1 image signal by a gain corresponding to the oxygen saturation for each pixel. For example, in a pixel where the oxygen saturation is 60% or more, the image generation section 79 multiplies all of the B1 image signal, the G1 image signal, and the R1 image signal by the same gain "1". In contrast, in a pixel where the corrected oxygen saturation is less than 60%, the image generation section 79 multiplies the B1 image signal by the gain less than "1" and multiplies the G1 image signal and the R1 image signal by the gain of "1" or more using the value of the oxygen saturation. The color image using the B1 image signal, the G1 image signal, and the R1 image signal after the gain processing is an oxygen saturation image. Therefore, in the oxygen saturation image, a high oxygen pixel (pixel with oxygen saturation of 60% to 100%) is expressed in the same color as the normal image, and a low oxygen pixel (pixel with oxygen saturation less than 60%) is expressed in a different color (pseudo-color) from the normal image.

Although the image generation section 79 performs gain multiplication for pseudo-coloring only the low oxygen pixel in the present embodiment, a gain corresponding to the oxygen saturation may also be multiplied for the high oxygen pixel so that the entire oxygen saturation image is pseudo-colored. In addition, although the reference oxygen saturation for division into the low oxygen pixel and the high oxygen pixel is 60%, the boundary is arbitrary.

The normal image generated as described above by the normal image generation unit 62 and the oxygen saturation image generated as described above by the oxygen saturation image generation unit 64 are input to the video signal generation unit 66. The video signal generation unit 66 converts the normal image or the oxygen saturation image into a video signal so that the normal image or the oxygen saturation image can be displayed on the monitor 18. Using the video signal, the monitor 18 displays the normal image and the oxygen saturation image thereon.

Figure 15:
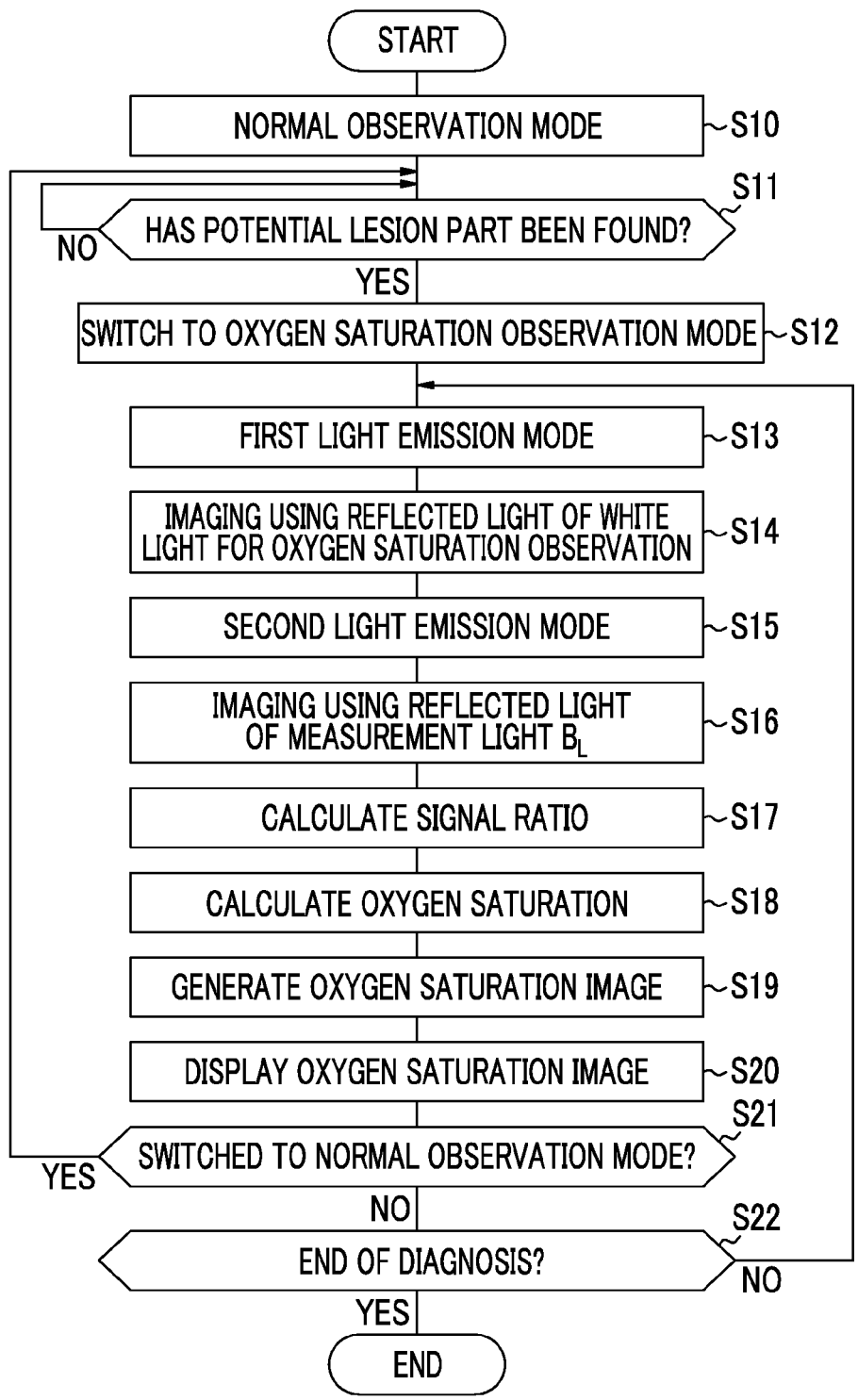
FIG. 15 is a flowchart of a first embodiment.

Next, a series of flow in the present embodiment will be described with reference to the flowchart shown in FIG. 15. First, in the normal observation mode, screening is performed from the long-distance view state (S10). When a part that is likely to be a lesion (hereinafter, referred to as a potential lesion part), such as a brownish area or rubor, is found in this screening (S11), enlargement observation to display the observation target including the potential lesion part in an enlarged manner is performed by operating the zoom operation section 13b. In accordance with this, the observation mode is switched to the oxygen saturation observation mode by operating the mode selector SW 13a (S12).

When the observation mode is switched to the oxygen saturation observation mode, the light source control unit 22 arranges the LPF 21b of the band limiting unit 21 on the optical path of the B-LED 20b first. Then, the light source control unit 22 controls the light source unit 20 in the first light emission mode to irradiate the observation target with the white light for oxygen saturation observation configured to include the violet light V, the measurement light $B_L$, the green light G, and the red light R (S13: first light source control step). Then, the imaging sensor 48 images the observation target with the reflected light of the white light for oxygen saturation observation, and outputs the B1 image signal, the G1 image signal, and the R1 image signal (S14: the first imaging step).

Thereafter, the light source control unit 22 switches the light emission mode automatically, and controls the light source unit 20 in the second light emission mode to irradiate the observation target with the measurement light $B_L$ (S15: second light source control step). Then, the imaging sensor 48 images the observation target with the reflected light of the measurement light $B_L$, and outputs the B2 image signal (S16: second imaging step).

After the B1 image signal, the G1 image signal, and the R1 image signal are obtained by imaging the observation target with the reflected light of the illumination light in the first light emission mode and the B2 image signal is obtained by imaging the observation target with the reflected light of the measurement light $B_L$ in the second light emission mode as described above, the oxygen saturation image generation unit 64 calculates the signal ratio B2/G1 and the signal ratio R1/G1 using the signal ratio calculation section 71 (S17: signal ratio calculation step), and calculates the oxygen saturation using the oxygen saturation calculation section 73 (S18: oxygen saturation calculation step). On the other hand, the oxygen saturation image generation unit 64 generates an image as a base of the oxygen saturation image by performing various kinds of image processing on the B1 image signal, the G1 image signal, and the R1 image signal using the color conversion processing section 76, the color enhancement processing section 77, and the structure enhancement processing section 78. Then, the image generation section 79 multiplies the B1 image signal, the G1 image signal, and the R1 image signal subjected to the various kinds of image processing by the gain corresponding to the oxygen saturation, and generates an oxygen saturation image using the B1 image signal, the G1 image signal, and the R1 image signal multiplied by the gain corresponding to the oxygen saturation (S19: image generation step). Steps S17 to S19 described above are an oxygen saturation image generation step. The oxygen saturation image generated as described above is converted into a video signal by the video signal generation unit 66, and an image obtained as a result is displayed on the monitor 18 (S20).

Figure 16:
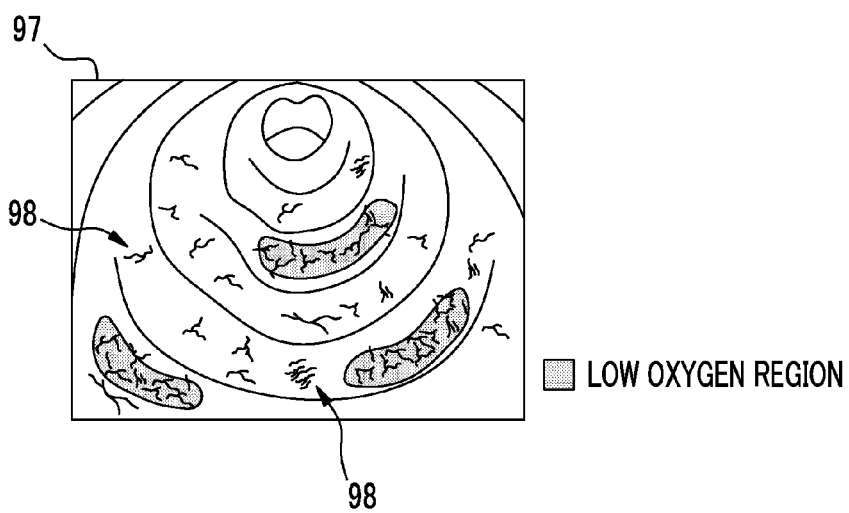
FIG. 16 is an explanatory diagram showing an oxygen saturation image.

As shown in FIG. 16, in an oxygen saturation image 97 generated and displayed as described above, a low oxygen pixel is displayed in a pseudo-color, and a fine structure 98 such as a superficial blood vessel or a pit pattern is clearly expressed. This is because the image as a base of the oxygen saturation image 97 is formed by the B1 image signal, the G1 image signal, and the R1 image signal, which are obtained by imaging the observation target with the reflected light of the illumination light in the first light emission mode, and the B1 image signal is formed by adding the signal value based on the reflected light of the blue light for normal observation $B_S$ and the signal value based on the reflected light of the violet light V and accordingly is an image signal with the good contrast of the fine structure 98. That is, in the endoscope system 10, an image signal that forms an image as a base of the oxygen saturation image is obtained by irradiating the observation target with not only the measurement light $B_L$ but also the white light for oxygen saturation observation obtained by adding the violet light V to the blue component. Accordingly, the accurate calculation of the oxygen saturation and the visibility of the fine structure 98 are compatible.

Each step in the oxygen saturation observation mode described above is repeatedly performed until the observation mode is switched to the normal observation mode (S21) or until the end of the diagnosis (S22). In addition, the observation flow described above is an example, and it is also possible to perform observation and diagnosis using the oxygen saturation observation mode in other flows. For example, although observation in the oxygen saturation observation mode is performed at the time of short-distance view observation in the observation flow described above, the observation using the oxygen saturation observation mode may also be performed at the time of long-distance view observation for screening or the like. In addition, although the observation target is imaged in the second light emission mode after imaging the observation target in the first light emission mode in the embodiment described above, it is also possible to image the observation target in the first light emission mode after imaging the observation target in the second light emission mode.

In the first embodiment described above, the white light for oxygen saturation observation is formed by the violet light V, measurement light $B_L$, the green light G, and the red light R in the first light emission mode. However, as is apparent from the operation of the endoscope system 10, the light source control unit 22 may form white light with light components of three colors of the measurement light $B_L$, the green light G, and the red light R and may form slightly violet light that is strong in blue as a whole, as illumination light in the first light emission mode, by adding the violet light V to the white light. In this case, since a case where wavelength components (especially, the blue component) for acquiring the B1 image signal are insufficient is unlikely to occur even if the LPF 21b is used, it is possible to generate and display an oxygen saturation image that can be easily observed.

Figure 17:
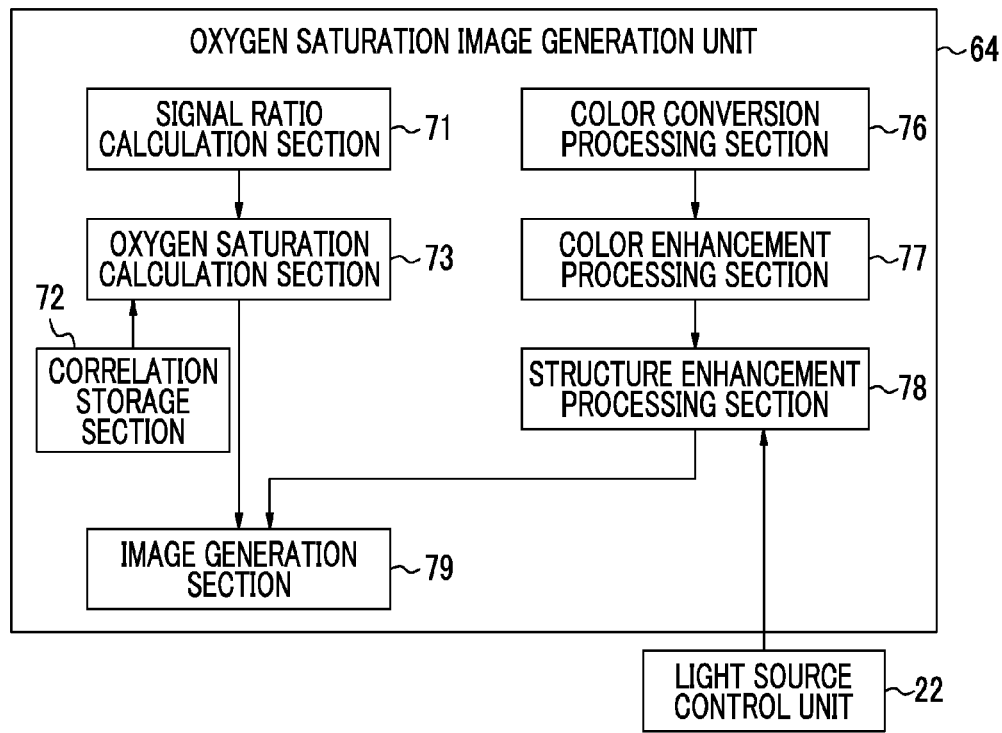
FIG. 17 is a block diagram when a structure enhancement processing section changes the degree of enhancement according to the amount of violet light.

Preferably, the structure enhancement processing section 78 provided in the oxygen saturation image generation unit 64 of the endoscope system 10 of the first embodiment described above acquires the information of the amount of violet light V in the first light emission mode from the light source control unit 22 and changes the degree of the structure enhancement processing using the amount of violet light V in the first light emission mode, as shown in FIG. 17. In this case, the light source control unit 22 inputs a value (lm, W, or the like) of the amount of violet light V or a control value (driving current, driving voltage, pulse width, or the like of the V-LED 20a) for controlling the V-LED 20a to the structure enhancement processing section 78 as the information of the amount of violet light V. Then, the structure enhancement processing section 78 increases the degree of the structure enhancement processing according to the information of the amount of violet light V input from the light source control unit 22, for example, as the amount of violet light V decreases. Thus, if the structure enhancement processing is performed based on the amount of violet light V, the visibility of superficial blood vessels and the like in the oxygen saturation image can be more easily maintained. Since the amount of violet light V is changed in order to enhance the visibility of superficial blood vessels and the like, if the degree of enhancement is changed so that the degree of the structure enhancement processing increases as the amount of violet light V increases contrary to the above, the visibility of superficial blood vessels and the like in the oxygen saturation image is likely to be particularly improved as necessary. The above is the same for an endoscope system of a second embodiment to be described below.

Second Embodiment

Figure 18:
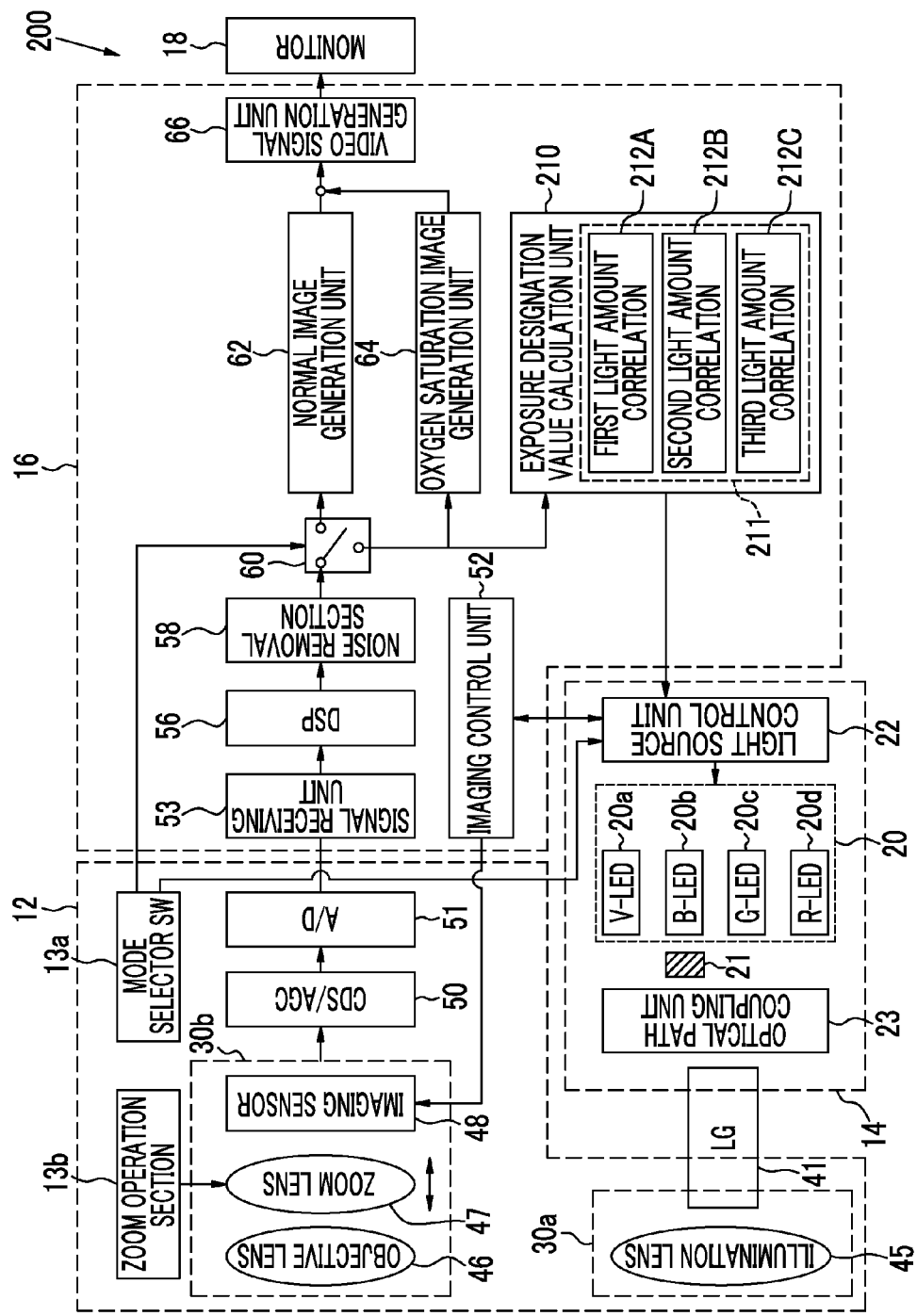
FIG. 18 is a block diagram showing the function of an endoscope system of a second embodiment.

An endoscope system 200 shown in FIG. 18 has the same configuration as the endoscope system 10 of the first embodiment except that an exposure designation value calculation unit 210 is added to the endoscope system 10 of the first embodiment.

The exposure designation value calculation unit 210 operates in the oxygen saturation observation mode, and acquires the B2 image signal from the image processing switching unit 60. In addition, using the B2 image signal, the exposure designation value calculation unit 210 calculates an exposure designation value for designating the amount of violet light V emitted from the V-LED 20a, the amount of blue light B emitted from the B-LED 20b, the amount of green light G emitted from the G-LED 20c, or the amount of red light R emitted from the R-LED 20d, in the first light emission mode.

In the present embodiment, the exposure designation value calculation unit 210 calculates an exposure designation value for designating the amount of blue light B emitted from the B-LED 20b in the first light emission mode using the average value of all pixels of the B2 image signal (hereinafter, referred to as an average value of the B2 image signal). The exposure designation value is for designating the amount of blue light B. However, since the LPF 21b is always disposed on the optical path of the B-LED 20b in the oxygen saturation observation mode, designating the amount of measurement light $B_L$ is the same as designating the amount of blue light B. The exposure designation value is calculated by multiplying the average value of the B2 image signal by a specific coefficient. The specific coefficient is set by experiment (or simulation) using the spectrum of the blue light B and the spectral characteristics of the SPF 21a and the LPF 21b of the band limiting unit 21.

The exposure designation value calculation unit 210 stores, in a storage unit 211, a first light amount correlation 212A obtained by associating the amount of violet light V with the amount of blue light B designated by the exposure designation value, a second light amount correlation 212B obtained by associating the amount of green light G with the amount of blue light B designated by the exposure designation value, and a third light amount correlation 212C obtained by associating the amount of red light R with the amount of blue light B designated by the exposure designation value. The first to third light amount correlations 212A, 212B, and 212C are set by experiment or the like, and are set such that an image signal, in which the white light for oxygen saturation observation serves as a base of an oxygen saturation image, is imaged with natural colors. The first to third light amount correlations 212A, 212B, and 212C are exposure ratios for calculating the amount of light of each color by multiplying the exposure designation value (the amount of blue light B) thereby. For example, the amount of violet light V is calculated by multiplying the amount of blue light B by the exposure ratio stored as the first light amount correlation 212A. This is the same for the amount of green light G and the amount of red light R.

Therefore, after calculating an exposure designation value for designating the amount of blue light B, the exposure designation value calculation unit 210 calculates an exposure designation value for violet light for designating the amount of violet light V, an exposure designation value for green light for designating the amount of green light and an exposure designation value for red light for designating the amount of red light R using the calculated exposure designation value and the calculated first to third light amount correlations 212A, 212B, and 212C.

The exposure designation value for designating the amount of blue light in the first light emission mode and the exposure designation value for each color for designating the amount of violet light V, the amount of green light G, and the amount of red light R are input to the light source control unit 22. The light source control unit 22 controls the amount of light of each of the LEDs 20a to 20d when controlling the light source unit 20 in the first light emission mode.

In the oxygen saturation observation mode, it is necessary to image the observation target under two types of different conditions of the first and second light emission modes. Accordingly, it is difficult to perform general automatic exposure adjustment that is performed when imaging the observation target continuously with the reflected light of white light. In particular, in the second light emission mode, only the measurement light $B_L$ is emitted to the observation target, and the green light G or the red light R is not included in the illumination light. Accordingly, it is difficult to calculate the brightness (average brightness of an image) as a reference in the general automatic exposure adjustment. For this reason, when imaging the observation target with the reflected light of the illumination light in the first light emission mode after imaging the observation target with the reflected light of the measurement light $B_L$ in the second light emission mode, it is difficult to appropriately set the amount of each color light component in the first light emission mode. When switching the light emission mode in the order of the first light emission mode, the second light emission mode, and the first light emission mode, it is possible to determine the amount of each color light component in the last first light emission mode in the sequence using the image signal obtained by imaging the observation target with the reflected light of the illumination light in the first light emission mode that is the first mode in the sequence. However, since the second light emission mode is interposed between the first light emission modes, there is a time interval therebetween. Therefore, accurate exposure adjustment may not be performed.

However, even in the oxygen saturation observation mode, only the blue image signal can be continuously acquired regardless of the light emission mode. In addition, not only the measurement light $B_L$ but also the violet light V is included in the white light for oxygen saturation observation in the first light emission mode. Accordingly, even though the B1 image signal obtained by imaging the observation target with the reflected light of the illumination light in the first light emission mode and the B2 image signal obtained from only the measurement light $B_L$ in the second light emission mode cannot be treated as the same signals, there is a certain correlation between the B1 image signal and the B2 image signal since the difference is only the amount of violet light V. Using this, if the amount of blue light B in the first light emission mode is set based on the B2 image signal obtained by imaging the observation target with the reflected light of the measurement light $B_L$ in the second light emission mode and the amount of violet light V, the amount of green light G, and the amount of red light R are further set based on the amount of blue light B as in the endoscope system 200 of the second embodiment described above, it is possible to perform accurate automatic exposure adjustment even if the first light emission mode is set after the second light emission mode.

In the second embodiment described above, the exposure designation value calculation unit 210 designates the amount of each color light component in the first light emission mode. Alternatively, it is also possible to designate the storage time of the imaging sensor 48 using the exposure designation value. The storage time is a time to accumulate signal charges in pixels by photoelectric conversion in order to obtain an image signal, and it is possible to adjust the exposure even by increasing or decreasing the storage time instead of changing the amount of light emitted to the observation target. Needless to say, the exposure designation value calculation unit 210 may adjust the exposure for acquiring an image signal by designating both of the amount of each color light component in the first light emission mode and the storage time of the imaging sensor 48. In this case, the exposure designation value calculation unit 210 calculates not only the exposure designation value for designating the amount of each color light component but also the exposure designation value for designating the storage time of the imaging sensor 48. The exposure designation value for designating the storage time may be a common value to RGB pixels. When the imaging sensor 48 can adjust the storage time of pixels of each color, different exposure designation values may be calculated for the RGB pixels.

In addition, although the exposure designation value calculation unit 210 designates the amount of each color light component in the first light emission mode using the B2 image signal obtained in the second light emission mode in the endoscope system 200 of the second embodiment described above, the exposure designation value calculation unit 210 may designate the amount of blue light B (and measurement light $B_L$) in the second light emission mode using the B1 image signal, the G1 image signal, or the R1 image signal obtained by imaging the observation target with the reflected light of the illumination light in the first light emission mode. For example, the exposure designation value calculation unit 210 calculates a second exposure designation value for designating the amount of blue light B in the second light emission mode by multiplying the average value of all pixels of the G1 image signal, which is obtained by imaging the observation target with the reflected light of the illumination light in the first light emission mode, by a second specific coefficient, and inputs the second exposure designation value to the light source control unit 22. If the amount of blue light B in the second light emission mode is adjusted using the G1 image signal as described above, the amount of measurement light $B_L$ in the second light emission mode is designated using the amount of green light G in the first light emission mode. Therefore, the light amount ratio between the green light G for acquiring the G1 image signal and the measurement light $B_L$ for acquiring the B2 image signal can be maintained in a certain relationship. Since the correlation between the signal ratio and the oxygen saturation is based on the assumption that the G1 image signal and the B2 image signal are obtained under specific conditions, it is possible to always maintain the state of high oxygen saturation calculation accuracy by maintaining the light amount ratio between the green light G in the first light emission mode and the blue light B in the second light emission mode in a certain relationship.

Also, when designating the amount of blue light B in the second light emission mode using the B1 image signal or the R1 image signal instead of G1 image signal, the light amount ratio between the green light G in the first light emission mode and the blue light B in the second light emission mode can be maintained indirectly in a certain relationship. Therefore, it is also possible to calculate the second light amount designation value for designating the amount of blue light B in the second light emission mode using the B1 image signal or the R1 image signal. As described above, the B1 image signal and the B2 image signal are the same blue image signals, and there is a certain correlation between the B1 image signal and the B2 image signal. If the amount of blue light B in the second light emission mode is designated using the B1 image signal, the amount of measurement light $B_L$ in the second light emission mode is designated using the amount of violet light V and the amount of blue light B in the first light emission mode. Therefore, even when switching from the first light emission mode to the second light emission mode occurs, it is possible to stably adjust the exposure.

Instead of designating the amount of blue light B in the second light emission mode using the image signal obtained by imaging the observation target with the reflected light of the illumination light in the first light emission mode as described above, it is also possible to designate the storage time of the imaging sensor 48 when imaging the observation target with the reflected light of the measurement light $B_L$ in the second light emission mode. Needless to say, it is also possible to adjust the exposure in the second light emission mode by designating both of the amount of blue light B in the second light emission mode and the storage time of the imaging sensor 48 using the image signal obtained by imaging the observation target with the reflected light of the illumination light in the first light emission mode.

Figure 19:
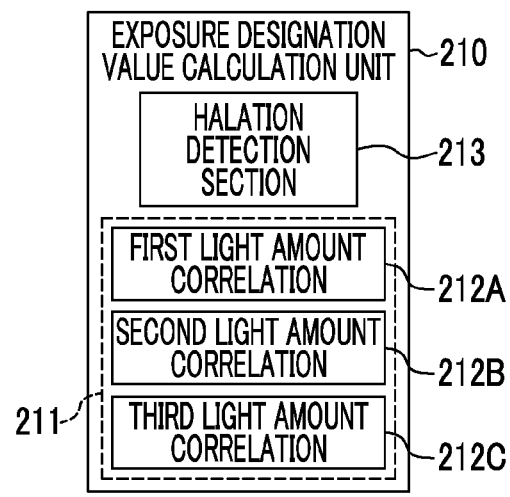
FIG. 19 is a block diagram of an exposure designation value calculation unit including a halation detection section.

In addition, it is preferable that the exposure designation value calculation unit 210 further includes a halation detection section 213, as shown in FIG. 19. The halation detection section 213 detects halation from the B2 image signal. The exposure designation value calculation unit 210 calculates an exposure designation value using the signal values of pixels other than a pixel in which halation is detected, instead of calculating the exposure designation value using all pixels of the B2 image signal. In this manner, it is possible to adjust the exposure more accurately. The above is the same for a case where the exposure is adjusted by the storage time of the imaging sensor 48 or a case where the amount of blue light B in the second light emission mode is designated using the B1 image signal, the G1 image signal, and the R1 image signal obtained by imaging the observation target with the reflected light of the illumination light in the first light emission mode.

In the endoscope systems 10 and 200 of the first and second embodiments described above, in the oxygen saturation observation mode, the light source control unit 22 controls the light source unit 20 in the first and second light emission modes. However, the light source control unit 22 controls the light source unit 20 alternately between the first and second light emission modes so as to match, for example, the imaging timing of the imaging sensor 48. In this manner, it is possible to update the oxygen saturation image displayed on the monitor 18 more quickly. In this case, the oxygen saturation image may be generated using the image signal obtained first in the first light emission mode and the B2 image signal obtained next in the second light emission mode, or the oxygen saturation image may be generated using the B2 image signal obtained first in the second light emission mode and the image signal obtained next in the first light emission mode, or the oxygen saturation image may be generated in both of these.

In addition to these, the number of times of the first light emission mode may be set to be larger than the number of times of the second light emission mode (for example, the first light emission mode, the first light emission mode, the second light emission mode, the first light emission mode, . . . ). Alternatively, the number of times of the second light emission mode may be set to be larger than the number of times of the first light emission mode. For example, when the number of times of the first light emission mode is set to be larger than the number of times of the second light emission mode, it is possible to obtain the oxygen saturation image with an enlarged dynamic range by generating the oxygen saturation image by adding a plurality of B1 image signals, a plurality of G1 image signals, and a plurality of R1 image signals obtained in a plurality of first light emission modes by changing the storage time of the imaging sensor 48 or the amount of white light for oxygen saturation observation in each first light emission mode. When the number of times of the second light emission mode is set to be larger than the number of times of the first light emission mode, it is possible to improve the oxygen saturation calculation accuracy by calculating the oxygen saturation by adding a plurality of B2 image signals obtained in a plurality of second light emission modes by changing the storage time of the imaging sensor 48 or the amount of measurement light $B_L$ in each second light emission mode.

In the first and second embodiments described above, in the second light emission mode, the B-LED 20b is turned on, and the V-LED 20a, the G-LED 20c, and the R-LED 20d are turned off. However, the amount of light emitted from the V-LED 20a, the G-LED 20c, and the R-LED 20d may be set to the minimum value instead of turning off the V-LED 20a, the G-LED 20c, and the R-LED 20d, so that the observation target is irradiated with substantially only the measurement light $B_L$. In this case, since a state where the V-LED 20a, the G-LED 20c, and the R-LED 20d are turned on even in the second light emission mode is maintained, it is possible to reduce the noise due to the transient phenomenon according to ON/OFF of each LED.

Figure 20:
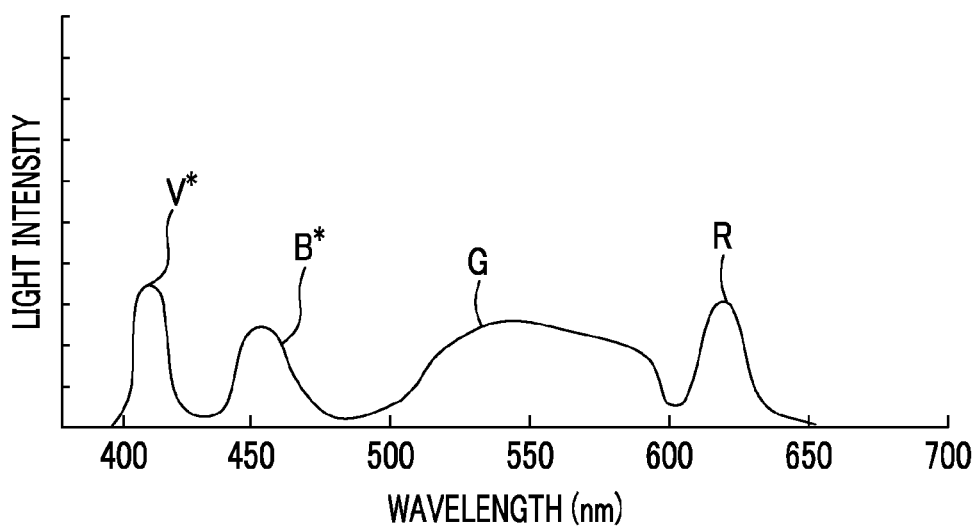
FIG. 20 is a graph showing the spectra of violet light and blue light that are different from those in FIG. 3.

Although the light components of four colors having the spectrum shown in FIG. 3 are used in the first and second embodiments described above, it is also possible to use light components of four colors having other spectra. For example, as shown in FIG. 20, the green light G and the red light R may have the same spectrum as in each embodiment described above, while light that has a center wavelength of 410 nm to 420 nm and a wavelength band on the slightly longer wavelength side than the violet light V in each embodiment described above, such as violet light V*, may be used as the violet light. In addition, for the blue light B, light that has a center wavelength of 445 nm to 460 nm and a wavelength band on the slightly shorter wavelength side than in each embodiment described above, such as blue light B*, may be used. The spectrum of illumination light shown in FIG. 3 or FIG. 20 is an example, and the relative amount of light emitted from the LEDs 20a to 20d may be changed according to the desired color or the like of the observed image. Specifically, it is possible to change the ratio of the amount of light emitted from the LEDs 20a to 20d by changing the driving current values or the like of the LEDs 20a to 20d.

In addition, as long as the blue light for normal observation $B_S$ and the measurement light $B_L$ are obtained, the characteristics of the SPF 21a and the LPF 21b provided in the band limiting unit 21 of the first and second embodiments may be arbitrary.

Figure 21:
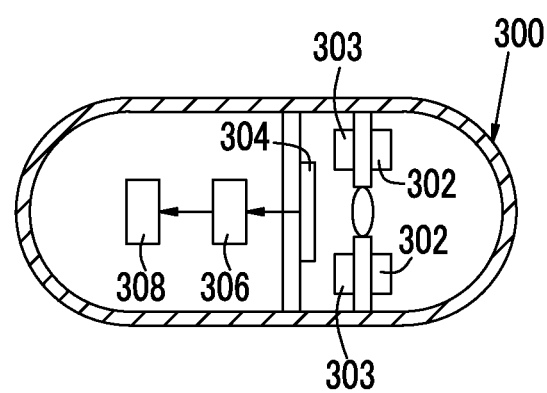
FIG. 21 is a schematic diagram of a capsule endoscope.

In addition, in the first and second embodiments described above, the invention is implemented by using the endoscope systems 10 and 200 that perform observation by inserting the endoscope 12 including the imaging sensor 48 into the subject. However, the invention is also suitable for a capsule endoscope system. For example, as shown in FIG. 21, a capsule endoscope system includes, at least, a capsule endoscope 300 and a processor device (not shown).

The capsule endoscope 300 includes a light source 302, a light source control unit 303, an imaging sensor 304, an oxygen saturation image generation unit 306, and a transmitting and receiving antenna 308. The light source 302 includes a V-LED that emits the violet light V, a B-LED that emits the blue light B, a G-LED that emits the green light G, an R-LED that emits the red light R, and a band limiting unit that generates the measurement light $B_L$ from the blue light B. The light source 302 corresponds to the light source unit 20 and the band limiting unit 21 of the first and second embodiments.

The light source control unit 303 controls the driving of the light source 302 in the same manner as the light source control unit 22 of the first and second embodiments. In addition, the light source control unit 303 can perform radio communication with the processor device of the capsule endoscope system through the transmitting and receiving antenna 308. Although the processor device of the capsule endoscope system is almost the same as the processor device 16 of the first and second embodiments, the oxygen saturation image generation unit 306 corresponding to the oxygen saturation image generation unit 64 is provided in the capsule endoscope 300, and the oxygen saturation image generated by the oxygen saturation image generation unit 306 is transmitted to the processor device through the transmitting and receiving antenna 308. The imaging sensor 304 is configured similarly to the imaging sensor 48 of the first and second embodiments.

What is claimed is:

1. An endoscope system, comprising an endoscope which has a distal portion provided with an illumination optical system, a light source device which is optically connected to the endoscope and a processor device which is electrically connected to the endoscope,
   wherein the light source device includes a light source unit including a violet light source that emits violet light, a blue light source that emits blue light, a green light source that emits green light, and a red light source that emits red light;
   a band limiter, having a short pass filter and a long pass filter, which is provided on the optical path of the blue light source, that generates measurement light having a specific wavelength band for measuring oxygen saturation from the blue light; and
   a light source controller that controls the light source unit in a first light emission mode, in which an observation target is irradiated with illumination light including the violet light, the green light and the red light emitted from the light source unit, and the measurement light generated by the band limiter, and a second light emission mode, in which the observation target is irradiated with the measurement light generated by the band limiter, and controls switching between the short pass filter and the long pass filter according to the first and second light emission modes;
   wherein the distal portion of the endoscope is provided with a color imaging sensor having a blue pixel for receiving the violet light and the measurement light, a green pixel for receiving the green light, and a red pixel for receiving the red light, through the illumination optical system;
   wherein the processor device is configured to image the observation target with reflected light of the illumination light including the violet light in the first light emission mode using the color imaging sensor and output a first blue image signal, a first green image signal, and a first red image signal from the color imaging sensor and image the observation target with reflected light of the measurement light in the second light emission mode using the color imaging sensor and output a second blue image signal from the color imaging sensor; and
   an oxygen saturation image generator that calculates oxygen saturation of the observation target using the second blue image signal and generates an oxygen saturation image showing the oxygen saturation of the observation target using the oxygen saturation, the first blue image signal, the first green image signal, and the first red image signal,
   wherein the oxygen saturation image generator generates the oxygen saturation image by performing structure enhancement processing for enhancing structures of the observation target, and changes a degree of the structure enhancement processing using the amount of violet light in the first light emission mode.

2. The endoscope system according to claim 1,
wherein a wavelength band of the blue light includes a wavelength at which absorption coefficients of oxygenated hemoglobin and reduced hemoglobin are the same, and
the specific wavelength band of the measurement light generated by the band limiter is a wavelength band in which the absorption coefficient of the oxygenated hemoglobin is equal to or greater than the absorption coefficient of the reduced hemoglobin, or a wavelength band in which the absorption coefficient of the oxygenated hemoglobin is equal to or less than the absorption coefficient of the reduced hemoglobin.

3. The endoscope system according to claim 2,
wherein, when controlling the light source unit in the second light emission mode, the light source controller turns on the blue light source and turns off the violet light source, the green light source, and the red light source, or reduces an amount of light of each of the violet light source, the green light source, and the red light source from an amount of light of each of the violet light source, the green light source, and the red light source in the first light emission mode in a state where the violet light source, the green light source, and the red light source are turned on.

4. The endoscope system according to claim 1,
wherein, when controlling the light source unit in the second light emission mode, the light source controller turns on the blue light source and turns off the violet light source, the green light source, and the red light source, or reduces an amount of light of each of the violet light source, the green light source, and the red light source from an amount of light of each of the violet light source, the green light source, and the red light source in the first light emission mode in a state where the violet light source, the green light source, and the red light source are turned on.

5. The endoscope system according to claim 1,
wherein the oxygen saturation image generator generates the oxygen saturation image by performing structure enhancement processing for enhancing structures of the observation target, and changes a degree of the structure enhancement processing using the amount of violet light in the first light emission mode.

6. The endoscope system according to claim 1,
wherein the light source controller forms white light with the measurement light, the green light, and the red light in the first light emission mode, adds the violet light to the white light, and irradiates the observation target with the white light including the violet light.

7. The endoscope system according to claim 1, wherein the processor device includes
an exposure designation value calculator that calculates an exposure designation value for designating the amount of violet light, the amount of measurement light, the amount of green light, and the amount of red light in the first light emission mode or a storage time of the color imaging sensor using the second blue image signal.

8. The endoscope system according to claim 7,
wherein the exposure designation value is a value for designating the amount of blue light in the first light emission mode using the second blue image signal, and
the exposure designation value calculator has a light amount correlation, which is obtained by associating the amount of violet light with the amount of blue light, and designates the amount of violet light using the light amount correlation and the amount of blue light designated by the exposure designation value.

9. The endoscope system according to claim 7,
wherein the exposure designation value is a value for designating the storage time of the color imaging sensor in the first light emission mode using the second blue image signal.

10. The endoscope system according to claim 7, further comprising:
a halation detection unit that detects halation using the second blue image signal,
wherein the exposure designation value calculator calculates the exposure designation value using signal values of pixels other than a pixel, in which the halation is detected, of the second blue image signal.

11. The endoscope system according to claim 1,
wherein the light source controller controls the light source unit alternately between the first and second light emission modes so as to match an observation target imaging timing of the color imaging sensor.

12. The endoscope system according to claim 1,
wherein the oxygen saturation image generator calculates the oxygen saturation using a plurality of the second blue image signals.

13. The endoscope system according to claim 1,
wherein the oxygen saturation image generator generates the oxygen saturation image using a plurality of the first blue image signals, a plurality of the first green image signals, and a plurality of the first red image signals.

14. The endoscope system according to claim 1,
wherein the violet light source emits violet light in a wavelength band of 380 nm to 420 nm that has a center wavelength of 405 nm.

15. A light source device optically connected to an endoscope, comprising:
a light source unit including a violet light source that emits violet light, a blue light source that emits blue light, a green light source that emits green light, and a red light source that emits red light;
a band limiter having a short pass filter and a long pass filter, which is provided on the optical path of the blue light source, that generates measurement light having a specific wavelength band for measuring oxygen saturation from the blue light; and
a light source controller that controls the light source unit in a first light emission mode, in which an observation target is irradiated with the violet light, the green light and the red light, emitted from the light source unit, and the measurement light generated by the band limiter, and a second light emission mode, in which the observation target is irradiated with the measurement light generated by the band limiter, and controls switching between the short pass filter and the long pass filter according to the first and second light emission modes.

16. The light source device according to claim 15,
wherein a wavelength band of the blue light includes a wavelength at which absorption coefficients of oxygenated hemoglobin and reduced hemoglobin are the same, and
the specific wavelength band of the measurement light generated by the band limiter is a wavelength band in which the absorption coefficient of the oxygenated hemoglobin is equal to or greater than the absorption coefficient of the reduced hemoglobin, or a wavelength band in which the absorption coefficient of the oxygenated hemoglobin is equal to or less than the absorption coefficient of the reduced hemoglobin.

17. The light source device according to claim 15,
wherein, when controlling the light source unit in the second light emission mode, the light source controller turns off the violet light source, the green light source, and the red light source.

18. The light source device according to claim 15,
wherein, when controlling the light source unit in the second light emission mode, the light source controller reduces an amount of light of each of the violet light source, the green light source, and the red light source from an amount of light of each of the violet light source, the green light source, and the red light source in the first light emission mode in a state where the violet light source, the green light source, and the red light source are turned on.

19. The light source device according to claim 15,
wherein the violet light source emits violet light in a wavelength band of 380 nm to 420 nm that has a center wavelength of 405 nm.

20. An operation method for an endoscope system including an endoscope which has a distal portion provided with an illumination optical system, a light source device which is optically connected to the endoscope and a processor device which is electrically connected to the endoscope, wherein the light source device includes a light source unit that includes a violet light source that emits violet light, a blue light source that emits blue light, a green light source that emits green light, and a red light source that emits red light and a band limiter, having a short pass filter and a long pass filter, which is provided on the optical path of the blue light source, that generates measurement light having a specific wavelength band for measuring oxygen saturation from the blue light, the operation method comprising:
a first light source control step in which a light source controller controls the light source unit in a first light emission mode in which an observation target is irradiated with illumination light including the violet light, the green light, and the red light emitted from the light source unit, and the measurement light generated by the band limiter;
a first imaging step in which a color imaging sensor having a blue pixel for receiving the violet light and the measurement light, a green pixel for receiving the green light, and a red pixel for receiving the red light images the observation target with reflected light of the illumination light in the first light emission mode and outputs a first blue image signal, a first green image signal, and a first red image signal;
a second light source control step in which the light source controller controls the light source unit in a second light emission mode in which the observation target is irradiated with the measurement light;
a second imaging step in which the color imaging sensor images the observation target with reflected light of the measurement light in the second light emission mode and outputs a second blue image signal; and
an oxygen saturation image generation step in which an oxygen saturation image generator calculates oxygen saturation of the observation target using the second blue image signal and generates an oxygen saturation image showing the oxygen saturation of the observation target using the oxygen saturation, the first blue image signal, the first green image signal, and the first red image signal,
wherein the oxygen saturation image generator generates the oxygen saturation image by performing structure enhancement processing for enhancing structures of the observation target, and changes a degree of the structure enhancement processing using the amount of violet light in the first light emission mode.

21. An operation method for a light source device optically connected to an endoscope including a light source unit that includes a violet light source that emits violet light, a blue light source that emits blue light, a green light source that emits green light, and a red light source that emits red light and a band limiter, having a short pass filter and a long pass filter, which is provided on the optical path of the blue light source, that generates measurement light having a specific wavelength band for measuring oxygen saturation from the blue light, the operation method comprising:
a first light source control step in which a light source controller controls the light source unit in a first light emission mode in which an observation target is irradiated with the violet light, the green light and the red light, emitted from the light source unit, and the measurement light generated by the band limiter; and
a second light source control step in which the light source controller controls the light source unit in a second light emission mode in which the observation target is irradiated with the measurement light generated by the band limiter.

* * * * *